United States Patent [19]

Schreiber et al.

[11] Patent Number: 5,731,155
[45] Date of Patent: *Mar. 24, 1998

[54] COMPOSITIONS FOR INHIBITION OF INTRACELLULAR TRANSCRIPTION FACTORS AND METHODS THEREFOR

[75] Inventors: Robert D. Schreiber, St. Louis, Mo.; Michael A. Farrar, Seattle, Wash.; Andrew C. Greenlund, St. Louis, Mo.

[73] Assignee: Washington University, St. Louis, Mo.

[*] Notice: The term of this patent shall not extend beyond the expiration date of Pat. No. 5,463,023.

[21] Appl. No.: 633,772

[22] PCT Filed: Oct. 21, 1994

[86] PCT No.: PCT/US94/12095

§ 371 Date: Jul. 2, 1996

§ 102(e) Date: Jul. 2, 1996

[87] PCT Pub. No.: WO95/11312

PCT Pub. Date: Apr. 27, 1995

Related U.S. Application Data

[63] Continuation-in-part of Ser. No. 141,499, Oct. 22, 1993, Pat. No. 5,463,023.

[51] Int. Cl.$^6$ .............................. C07K 7/00; C07K 7/04; G01N 33/53
[52] U.S. Cl. ........................... 435/7.1; 530/327; 530/330
[58] Field of Search ........................ 435/6, 7.1, 172.1, 435/172.3; 530/324, 325, 326, 327, 328, 329, 350

[56] References Cited

U.S. PATENT DOCUMENTS 5,463,023 10/1995 Schreiber et al. ...................... 530/327

OTHER PUBLICATIONS

Ceresa et al., J. Biol. Chem., vol. 271, No. 21, pp. 12121–12124, May 24, 1996.

Karras et al., J. Immunol., vol. 157, No. 6, pp. 2299–2309, Sep. 1996.

Kim et al., Science, vol. 273, pp. 1717–1719, 20 Sep. 1996.

Aguet et al., (1988), Molecular Cloning and Expression of the Human Interferon–X Receptor, Cell 55:273–80.

Farrar et al., (1991), Identification of Two Regions within the Cytoplasmic Domain of the Human Interferon–γ Receptor Required for Function, The Journal of Biological Chemistry 266:19626–19635.

Farrar et al., (1992), Identification of a functionally important sequence in the C terminus of the inteferon–γ receptor, Proc. Natl. Acad. Sci. 89:11706–10.

Schindler et al., (1992), Proteins of transcription factor ISGF-3: One gene encodes the 91–and 84–kDa ISGF-3 proteins that are activated by interferon α, Proc. Natl. Acad. Sci. 89:7836–9.

Fu, (1992), A Transcription Factor with SH2 and SH3 Domains Is Directly Activated by an Interferon α–Induced Cytoplasmic Protein Tyrosine Kinase(s) Cell 70:323–35.

Wilson et al., (1992), Interferon γ rapidly induces in human monocytes a DNA–binding factor that recognizes the γ response region within the promoter of the gene for the high–affinity Fcγ receptor, Proc. Natl. Acad. Sci. 89:11964–8.

Greenlund et al., (1993), Interferon–γ Induces Receptor Dimerization in Solution and on Cells, Journal of biological Chemistry 268:18103–10.

Igarashi et al., (1993), In Vitro Activation of the Transcription Factor Gamma Interferon Activation Factor by Gamma Interferon: Evidence for a Tyrosine Phosphatase/Kinase Signaling Cascade, Molecular and Cellular Biology 13:1634–40.

Igarashi et al., (1993), In Vitro Activation of a Transcription Factor by Gamma Interferon Requires a Membrane–Associated Tyrosine Kinase and Is Mimicked by Vanadate, Molecular and Cellular Biology 13:3984–9.

Pearse et al., (1993) Interferon γ–induced transcription of the high–affinity Fc receptor for IgG requires assembly of a complex that includes the 91–kDa subunit of transcription factor ISGF3, Proc. Natl. Acad. Sci. 90:4314–18.

Schindler et al., (1992), Interferon–Dependent Tyrosine Phosphorylation of a Latent Cytoplasmic Transcription Factor, Science 257:809–13.

Fu et al., (1992), The proteins of ISGF-3, the interferon α–induced transcriptional activator, define a gene family involved in signal transduction, Proc. Natl. Acad. Sci. 89:7840–43.

Bandyopadhyay et al., (1992), Role of Protein Phosphorylation in Activation of Interferon–stimulated Gene Factors, The Journal of Biological Chemistry 267:6389–95.

(List continued on next page.)

Primary Examiner—David Guzo
Attorney, Agent, or Firm—Howell & Haferkamp, L.C.

[57] ABSTRACT

Novel compositions and methods for inhibiting cytokine-induced intracellular activation of STAT family transcription factors by binding to the transcription factors and inhibiting the transcriptional activity of the factors are disclosed. The method comprises introducing into a cell an effective amount of a peptide or derivative thereof, in which the peptide contains a sequence that is derived from a receptor for the cytokine, but with a tyrosine residue being phosphorylated. The compositions comprise isolated peptides or derivatives thereof in which the peptide contains an amino acid sequence derived from a receptor for a cytokine but with a tyrosine residue phosphorylated. A method for identifying derivatives of the isolated peptides comprising detecting the inhibition of the binding of said peptide to a STAT family transcription factor by said derivative is also provided.

8 Claims, 17 Drawing Sheets

OTHER PUBLICATIONS

David et al., (1993), In Vitro Activation of the Transcription Factor ISGF3 by Interferon α involves a Membrane-associated Tyrosine Phosphatase and Tyrosine Kinase, *The Journal of Biological Chemistry* 268:6593–99.

Shuai et al., (1992), Activation of Transcription by IFN-γ: Tyrosine Phosphorylation of a 91–kD DNA Binding Protein, *Science* 258:1808–12.

Suke Yue Hoo et al., (1993), A Receptor for Interleukin 10 is Related to Interferon Receptors, *Proc. Natl. Acad. Sci. USA* 90:11267–11271.

Hou et al., (1994), An Interleukin–4–Induced Transcription Factor: IL–4 Stat, *Science* 265:1701–1706.

Burke, Jr. et al., (1994), Nonydrolyzable Phsphotyrosyl Mimetics for the Preparation of Phosphatase–Resistant SH2 Domain Inhibitors, *Biochem.* 33:6490–6494.

Ihle et al., (1994), Signaling by the Cytokine Receptor Superfamily: JAKs and STATs, *TIBS* 19:222–227.

Hunter, (1993), Cytokine Connections, *Nature* 366:114–116.

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Modified-site
        ( B ) LOCATION: 1
        ( D ) OTHER INFORMATION: /note=phosphorylated tyrosine ( i x ) FEATURE:
        ( A ) NAME/KEY: Modified-site
        ( B ) LOCATION: 3
        ( D ) OTHER INFORMATION: /note= any amino acid ( i x ) FEATURE:
        ( A ) NAME/KEY: Modified-site
        ( B ) LOCATION: 4
        ( D ) OTHER INFORMATION: /note= any amino acid ( x i ) SEQUENCE DESCRIPTION: SEQ ID NO:1:

Xaa  Asp  Xaa  Xaa  His
    1                           5

( 2 ) INFORMATION FOR SEQ ID NO:2:

( i ) SEQUENCE CHARACTERISTICS:
        ( A ) LENGTH: 5 amino acids (B) TYPE: amino acid
(C) STRANDEDNESS: Not Relevant
(D) TOPOLOGY: Not Relevant (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

Tyr Asp Lys Pro His
1               5

(2) INFORMATION FOR SEQ ID NO:3:

(i) SEQUENCE CHARACTERISTICS:
(A) LENGTH: 9 amino acids
(B) TYPE: amino acid
(C) STRANDEDNESS: Not Relevant
(D) TOPOLOGY: Not Relevant (ii) MOLECULE TYPE: peptide (iii) HYPOTHETICAL: NO (iv) ANTI-SENSE: NO (v) FRAGMENT TYPE: internal (ix) FEATURE:
(A) NAME/KEY: Modified-site
(B) LOCATION: 5
(D) OTHER INFORMATION: /note=phosphorylated tyrosine (xi) SEQUENCE DESCRIPTION: SEQ ID NO:3:

Thr Ser Phe Gly Xaa Asp Lys Pro His
1               5

(2) INFORMATION FOR SEQ ID NO:4:

(i) SEQUENCE CHARACTERISTICS:
(A) LENGTH: 12 amino acids
(B) TYPE: amino acid
(C) STRANDEDNESS: Not Relevant
(D) TOPOLOGY: Not Relevant (ii) MOLECULE TYPE: peptide (iii) HYPOTHETICAL: NO (iv) ANTI-SENSE: NO (v) FRAGMENT TYPE: internal (ix) FEATURE:
(A) NAME/KEY: Modified-site
(B) LOCATION: 5
(D) OTHER INFORMATION: /note=phosphorylated tyrosine (xi) SEQUENCE DESCRIPTION: SEQ ID NO:4:

Thr Ser Phe Gly Xaa Asp Lys Pro His Val Leu Val
1               5                   10

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: other nucleic acid (i i i) HYPOTHETICAL: NO (i v) ANTI-SENSE: NO (x i) SEQUENCE DESCRIPTION: SEQ ID NO:5:

CCTCCTTTGG TTTTGATAAA C    21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (i v) ANTI-SENSE: NO (x i) SEQUENCE DESCRIPTION: SEQ ID NO:6:

GTTTATCAAA ACCAAAGGAG G    21

(2) INFORMATION FOR SEQ ID NO:7:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (i v) ANTI-SENSE: NO (x i) SEQUENCE DESCRIPTION: SEQ ID NO:7:

TGTATCACTC ATCACGTCAT TCCAGCCATT TTCGTTAGAA AAGG    44

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (i v) ANTI-SENSE: NO (x i) SEQUENCE DESCRIPTION: SEQ ID NO:8:

ATGACGTGAT GAGTGATACA AATTTTGATT CAGG    34

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO ( i v ) ANTI-SENSE: NO ( x i ) SEQUENCE DESCRIPTION: SEQ ID NO:9:

CGCTTTGAAC TCGTTTCAAT ACAG  24

( 2 ) INFORMATION FOR SEQ ID NO:10:

( i ) SEQUENCE CHARACTERISTICS:
       ( A ) LENGTH: 27 base pairs
       ( B ) TYPE: nucleic acid
       ( C ) STRANDEDNESS: single
       ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:10:

CTGGAGTGAA ACGAGTTCAA AGCGATG  27

( 2 ) INFORMATION FOR SEQ ID NO:11:

( i ) SEQUENCE CHARACTERISTICS:
       ( A ) LENGTH: 52 base pairs
       ( B ) TYPE: nucleic acid
       ( C ) STRANDEDNESS: single
       ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:11:

CCATCGATGT CATGAAAATT CTTTGGAATC TTCTGTTGGT CTAAAACCAA TC  52

( 2 ) INFORMATION FOR SEQ ID NO:12:

( i ) SEQUENCE CHARACTERISTICS:
       ( A ) LENGTH: 16 base pairs
       ( B ) TYPE: nucleic acid
       ( C ) STRANDEDNESS: single
       ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:12:

ATGTATTTCC CAGAAA  16

( 2 ) INFORMATION FOR SEQ ID NO:13:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:13:

CTTTTCTGGG AAATA 15

( 2 ) INFORMATION FOR SEQ ID NO:14:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:14:

GATCCATGCC TCGGGAAAGG GAAACCGAAA CTGAAGCCAC 40

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:15:

Thr Ser Phe Gly Tyr Asp Lys Pro His
1               5

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Modified-site
        ( B ) LOCATION: 5
        ( D ) OTHER INFORMATION: /note=phosphorylated tyrosine ( x i ) SEQUENCE DESCRIPTION: SEQ ID NO:16:

Thr Ser Phe Gly Xaa Ala Lys Pro Ala
1               5

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: Not Relevant ( i i ) MOLECULE TYPE: peptide (iii) HYPOTHETICAL: NO (iv) ANTI-SENSE: NO (v) FRAGMENT TYPE: internal (ix) FEATURE:
(A) NAME/KEY: Modified-site
(B) LOCATION: 5
(D) OTHER INFORMATION: /note=phosphorylated tyrosine (xi) SEQUENCE DESCRIPTION: SEQ ID NO:17:

```
Ser Leu Ile Gly Xaa Arg Pro Thr Glu Asp Ser Lys
1               5                   10
```

(2) INFORMATION FOR SEQ ID NO:18:

(i) SEQUENCE CHARACTERISTICS:
(A) LENGTH: 12 amino acids
(B) TYPE: amino acid
(C) STRANDEDNESS: Not Relevant
(D) TOPOLOGY: Not Relevant (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:18:

```
Thr Ser Phe Gly Tyr Asp Lys Pro His Val Leu Val
1               5                   10
```

(2) INFORMATION FOR SEQ ID NO:19:

(i) SEQUENCE CHARACTERISTICS:
(A) LENGTH: 12 amino acids
(B) TYPE: amino acid
(C) STRANDEDNESS: Not Relevant
(D) TOPOLOGY: Not Relevant (ii) MOLECULE TYPE: peptide (iii) HYPOTHETICAL: NO (iv) ANTI-SENSE: NO (v) FRAGMENT TYPE: internal (ix) FEATURE:
(A) NAME/KEY: Modified-site
(B) LOCATION: 5
(D) OTHER INFORMATION: /note=phosphorylated tyrosine (xi) SEQUENCE DESCRIPTION: SEQ ID NO:19:

```
Thr Ser Phe Gly Xaa Ala Lys Pro Ala Val Leu Val
1               5                   10
```

(2) INFORMATION FOR SEQ ID NO:20:

(i) SEQUENCE CHARACTERISTICS:
(A) LENGTH: 5 amino acids
(B) TYPE: amino acid
(C) STRANDEDNESS: Not Relevant
(D) TOPOLOGY: Not Relevant (ii) MOLECULE TYPE: peptide (iii) HYPOTHETICAL: NO (iv) ANTI-SENSE: NO (v) FRAGMENT TYPE: internal (ix) FEATURE:
            (A) NAME/KEY: Modified-site
            (B) LOCATION: 1
            (D) OTHER INFORMATION: /note=phosphorylated tyrosine (xi) SEQUENCE DESCRIPTION: SEQ ID NO:20:

Xaa Gln Lys Gln Thr
    1               5

(2) INFORMATION FOR SEQ ID NO:21:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: internal (ix) FEATURE:
            (A) NAME/KEY: Modified-site
            (B) LOCATION: 1
            (D) OTHER INFORMATION: /note=phosphorylated tyrosine (xi) SEQUENCE DESCRIPTION: SEQ ID NO:21:

Xaa Leu Lys Gln Glu
    1               5

(2) INFORMATION FOR SEQ ID NO:22:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:22:

Tyr Gln Lys Gln Thr
    1               5

(2) INFORMATION FOR SEQ ID NO:23:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:23:

```
        Tyr Leu Lys Gln Glu
        1               5
```

( 2 ) INFORMATION FOR SEQ ID NO:24:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Modified-site
        ( B ) LOCATION: 5
        ( D ) OTHER INFORMATION: /note=phosphorylated tyrosine ( x i ) SEQUENCE DESCRIPTION: SEQ ID NO:24:

```
        Thr Phe Gln Gly Xaa Gln Lys Gln Thr Arg Arg Trp Lys
        1               5               10
```

( 2 ) INFORMATION FOR SEQ ID NO:25:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Modified-site
        ( B ) LOCATION: 5
        ( D ) OTHER INFORMATION: /note=phosphorylated tyrosine ( x i ) SEQUENCE DESCRIPTION: SEQ ID NO:25:

```
        Leu Ala Ala Gly Xaa Leu Lys Gln Glu Ser Ser Gln Gln
        1               5               10
```

COMPOSITIONS FOR INHIBITION OF INTRACELLULAR TRANSCRIPTION FACTORS AND METHODS THEREFOR

This application is a 371 of PCT/US94/12095, filed Oct. 21, 1994 and a Continuation-in-part of Ser. No. 08/141,499, filed Oct. 22, 1993, now U.S. Pat. No. 5,463,023.

This invention was made with Government support under Grant No. CA 43059 awarded by the National Institutes of Health. The Government has certain rights in the invention.

BACKGROUND OF THE INVENTION

(1) Field of the Invention

This invention relates in general to the activity of cytokines that utilize the STAT family of transcription factors for inducing cellular responses including interferonγ (IFNγ), interleukin-10 (IL-10) and the like, and more particularly to a composition capable of the intracellular inhibition of a cytokine-activatable STAT-family transcription factor that is involved in the activation of genes inducible by the cytokine, and to methods for inhibiting such a transcription factor.

(2) Description of Background Art

Cytokines are a group of regulatory polypeptides involved in the inductive and effector phases of immunologic and inflammatory responses. High affinity cell surface receptors bind the cytokine molecules and this event is converted into an intracellular signal that is transmitted to the nucleus. This membrane-to-nucleus, transduction pathway almost universally involves tyrosine phosphorylation of one or more transcription factors. (Hunter, *Nature* 366:114–116 which is incorporated by reference).

One family of latent cytoplasmic proteins that serve as cytokine transcription factors has been termed STAT (signal transducers and activators of transcription). There are six known members of the STAT family, STAT 1 (p91), STAT 2 (p113), STAT3 (APRF), STAT 4, STAT 5 (MGF) and IL-4 STAT. (Hou et al., *Science* 265:1701–1706, 1994 which is incorporated by reference). The STAT family of transcription factors share some sequence similarities. These include a carboxy-terminal SH3 domain followed by an SH2 domain; homologous regions in the amino-terminal region; and a conserved tyrosine near the carboxy terminus that is phosphorylated and is essential for function. (Ihle et al., *TIBS* 19:222–227, 1994; Shuai et al. *Science* 261:1744–1746, 1994 which are incorporated by reference). The STAT transcription factors become activated through phosphorylation of tyrosine residues. The STAT proteins are then translocated to the nucleus in homodimeric or in heterocomplexed form. Here they bind to specific sequences or response elements and stimulate transcription. (for review see Darnell et al., *Science* 264:1415–1421. 1994 which is incorporated by reference). The cytokine-induced Intracellular signal transduction by STAT family members is exemplified by studies with Interferonγ (IFNγ) and Interleukin-10 (IL-10).

Interferonγ is an important cytokine derived from T cells and natural killer cells that plays important roles in promoting host defense and immunopathologic processes. IFNγ exerts its pleiotropic effects on cells through an interaction with a specific high affinity receptor expressed at the cell surface. Functionally active receptors require the presence of two distinct species specific polypeptides: a 90 kDa α chain that is both necessary and sufficient for IFNγ binding and processing and necessary but not sufficient for biologic response induction, and a second recently cloned polypeptide now denoted as the IFNγ receptor β chain needed exclusively for development of functional responses in cells (Jung et al., 1987; Jung et al., 1990; Fischer et al., 1990; Farrar et al. 1991; Gibbs et al., 1991 all of which are incorporated by reference). Although the function of the receptor β chain remains unclear, the structure-function relationships that exist within the receptor α chain have been the focus of a number of recent studies (Farrar et al., 1991; Farrar et al., 1992 which is incorporated by reference). Specifically, these analyses have revealed two topographically distinct, functionally important regions within the receptor α chain's intracellular domain. The first is comprised of 48 amino acids, proximal to the receptor's transmembrane domain (amino acids 256–303), and contains elements required for both receptor-mediated ligand internalization and biologic response induction (enhancement of MHC class I expression) (Farrar et al., 1991 which is incorporated by reference). The second region is located near the receptor's carboxy terminus, distal to the transmembrane region, and includes three closely spaced amino acids, Y440, D441, and H444, which are required exclusively for biologic responsiveness (Farrar et al., 1992 which is incorporated by reference).

The increased understanding of the structure and function of the IFNγ receptor has coincided with an explosive growth in understanding of the intracellular molecular events that underlie IFNγ dependent signal transduction. Recently IFNγ has been shown to induce in cells the phosphorylation and activation of a latent SH2 domain containing cytoplasmic transcription factor, known as p91 or STAT1, a member of the STAT family of transcription factors. Activation of p91 effects the assembly of an active p91-containing multimolecular transcription factor complex which translocates to the nucleus and binds to specific sequences in the promoters of IFNγ inducible genes, thereby initiating gene transcription (Decker et al., 1991; Schindler et al., 1992; Fu et al., 1993; Shuai et al., 1993; Pearse et al., 1993 all of which are incorporated by reference).

IFNγ is also known to be a potent activator of monocytes and macrophages and is, therefore, a critical component for host defense and the inflammation response. The secretion of IFNγ elicits the induction of numerous genes that encode for proteins that can act as soluble, secreted mediators of inflammation, such as IL-8 and IP-10, and other receptor proteins that are crucial for immune responsiveness and host defense. IFNγ is, therefore, believed to contribute to the adverse effects of inflammatory diseases and autoimmune diseases because of its significant gene inducible characteristics.

Interleukin-10 (IL-10) is a major cytokine produced by a number of different cell types including T-helper cells, B cells, EBV-transformed lymphoblastoid cell lines and mononuclear phagocytes (de Waal Malefyt et al., *Current Opin Immun* 4:314–320, 1992 which is incorporated by reference). The homodimeric polypeptide, IL-10, produces diverse biological activities such as inhibition of the production of proinflammatory cytokines including IL-12, TNF, IL-1 and IFNγ and the enhancement of the growth of B cells and mast cells. (For reviews, see Howard et al. *J Clin Immunol* 12:239–,1993; de Waal Malefyt et al., supra both of which are incorporated by reference). The suppression of proinflamatory cytokines by IL-10 may constitute a cross-regulatory mechanism. IL-10 inhibits cytokine synthesis, especially IFNγ, and immune functions in T-helper class 1 cells. Furthermore, IFNγ produced by T-helper class 1 cells involved in delayed-type hypersensitivity responses inhibits proliferation of T-helper class 2 cells involved in mediating help for antibody production. (de Waal Malefyt et al., supra; Moore et al., *Ann Rev Immunol* 11:165–190, 1993 both of which are incorporated by reference). This regulatory interaction of cytokines may be involved in disease processes. It has been reported that whereas resistance to fatal infection from *T. cruzi* is importantly mediated by IFNγ, IL-10 inhibits the production of IFNγ and may also inhibit the effects of IFNγ thus mediating a susceptibility to the disease. (Silva et al *J. Exp. Med.* 175:169–74, 1992 which is incorporated by reference). It has also been shown that IL-10 decreases the production of IL-1, IL-6, IL-12 and tumor necrosis factor-α and that treatment with IL-10 can confer protection from lipopolysaccharide-induced shock which is thought to be mediated by the release of TNF-α and IL-1. (Howard et al. *J. Exp. Med.* 177:1205–1208, 1993 which is incorporated by reference).

The IL-10 receptor is constitutively expressed in low numbers on a restricted panel of cell types derived from hematopoietic origin. Recently, it was shown the IL-10 dependent activation of transcription involves the activation of the p91 transcription factor termed STAT1. In different cytokine systems, STAT1 activation results upon phosphorylation of cytokine receptors after receptor-ligand interaction. Association of STAT1 with the receptor leads to phosphorylation and consequent activation of the STAT protein. Homodimeric STAT1 or heterocomplexed STAT1-STAT2 are translocated to the nucleus and the transcription factor complexes initiate the transcription of genes which contain in their promoters similar sequences termed interferon activated sequences and interferon stimulated response elements. DNA sequences in the promoters of other genes like the SIE in the c-fos promoter have substantial similarity to the DNA consensus sequence of the interferony activated sequences. Accordingly, the STAT1 protein has been shown to be a component of the EGF-induced SIE-binding factor. These findings indicated that cytokines with diverse or even antagonizing biological activities like IL-10, IFNγ, IFNα, EGF and CNTF share common components in their signal transduction.

Recently, a transcription factor induced by Interleukin-4 (IL-4) in Thp-1 cells was reported. (Hou et al., supra). This group disclosed that two phosphopeptides derived from the intracellular domain of the IL-4 receptor displaced the binding of IL-4 STAT to a DNA probe derived from the gene encoding FcγRI. Relatively high concentrations (100–300 μM) were required. Furthermore, the disclosed tests evaluated the ability of the peptides to displace IL-4 STAT from the DNA probe, but no data was provided to indicate whether the peptides were able to inhibit activation of the IL-4 STAT by IL-4.

SUMMARY OF THE INVENTION

This invention encompasses novel compositions and methods that result in the inactivation of cytokine-inducible STAT-family transcription factors by binding to the transcription factor in the cell and inhibiting their activation, resulting in ablation of the induction of transcriptional activity of the factor. Because the membrane-to-nucleus transduction pathway for cytokines almost universally involves tyrosine phosphorylation of one or more transcription factors, the present invention is applicable to all cytokine-activatable STAT-family-member transcription factors.

In one embodiment, the present invention provides a composition comprising an isolated peptide containing the amino acid sequence Xaa$_1$-Asp-Xaa$_2$-Xaa$_3$-His (SEQ ID NO:1) where Xaa$_1$ is a phosphorylated tyrosine and Xaa$_2$ and Xaa$_3$ are any amino acids, capable of specifically binding to the p91 family of IFNγ inducible transcription factors in a cell. This amino acid sequence is based on residues 440–444 of the IFNγ receptor α chain. Other suitable peptides can be designed containing all or part of the 5 amino acid sequence of SEQ ID NO:1 so long as Xaa$_1$ is a phosphorylated tyrosine and the peptides are capable of binding to a member of the p91 family of IFNγ inducible transcription factors. The specific binding activity of a phosphorylated peptide containing the peptide sequence of SEQ ID NO:1 was demonstrated by comparison with a non-phosphorylated peptide having the same sequence which showed little or no capacity to bind to a p91 transcription factor.

In another embodiment, the present invention provides a composition comprising an isolated peptide containing the amino acid sequence Xaa-Gln-Lys-Gln-Thr (SEQ ID NO:20) where Xaa is a phosphorylated tyrosine and the amino acid sequence Xaa-Leu-Lys-Gln-Glu (SEQ ID NO:21) where Xaa is a phosphorylated tyrosine. These compositions are capable of specifically binding and inactivating the 92 kD, STAT3 transcription factor that is inducible by IL-10. These amino acid sequences are based upon residues 427–431 and 477–481 of the IL-10 receptor (Hoet al., *Proc Natl Acad Sci* 90:11267–11271, 1993 which is incorporated by reference). Other suitable peptides can be designed containing all or part of the 5 amino acid sequence of SEQ ID NO:20 or SEQ ID NO:21 so long as Xaa is a phosphorylated tyrosine and the peptides are capable of binding to the STAT3 transcription factor.

Both peptide and non-peptide derivatives of the proteins can also be prepared that exhibit the functionality of being capable of binding to the transcription factors and inhibiting the transcriptional activity in a cell.

In another embodiment of the present invention a method is provided for identifying nonpeptide analogues that are peptidomimetics of the polypeptides wherein the nonpeptide analogues are capable of binding and inactivating the transcription factors.

In another embodiment of the present invention, a method is provided for inhibiting the intracellular activation of a transcription factor by introducing into a cell an effective amount of a peptide that contains the 5 amino acid sequence of SEQ ID NO:1 or SEQ ID NO:20 or SEQ ID NO:21 or a derivative of SEQ ID NO:1 or SEQ ID NO:20 or SEQ ID NO:21, wherein the derivative specifically binds to a transcription factor in the cell. The introduction of the exogenous peptide, or derivative thereof, into a cell causes the peptide to bind to the transcription factor and inhibit its transcriptional activity.

Among the several advantages found to be achieved by the present invention, therefore may be noted the provision of a composition that blocks the effect of IFNγ by binding and inactivating the STAT1 transcription factor; the provision of a composition that blocks the effect of IL-10 by binding and inactivating the STAT3 transcription factor; the provision of a method for isolating nonpeptide derivatives of the composition; and the provision of method for inhibiting the intracellular activation of a transcription factor by introducing into a cell an effective amount of a composition that binds to the transcription factor.

DETAILED DESCRIPTION OF THE INVENTION

Figure 1:
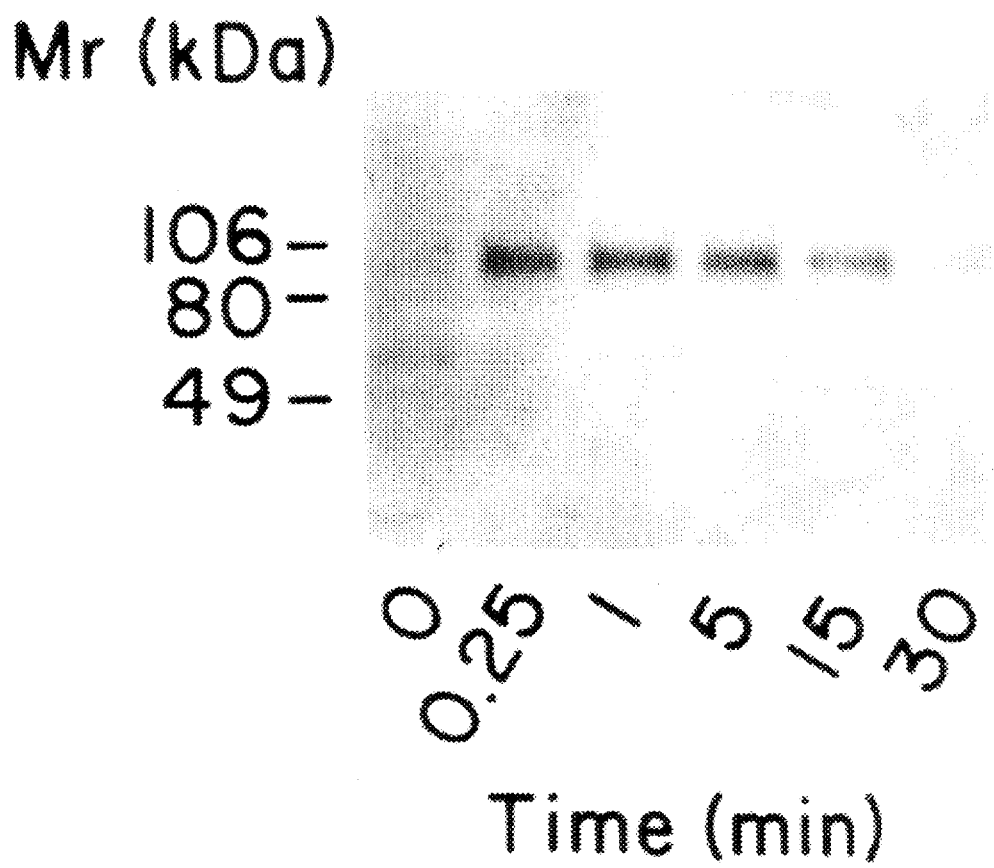
FIG. 1 is a western blot illustrating the kinetics of IFNγ receptor tyrosine phosphorylation.

In accordance with the present invention, it has been discovered that cytokine-inducible STAT-family transcription factors can be inhibited by the introduction of a composition capable of binding to the transcription factor in the cell. This approach results in the blocking of the cellular effect of the cytokine by uncoupling the membrane-to-nucleus signal transduction. Because of the almost universal nature of the utilization of tyrosine phosphorylation of transcription factors by cytokine systems, this discovery is applicable to nearly all cytokine-activated transcription factors.

The terms p91 family and STAT family of transcriptions denote the same transcription factors and are used interchangeably herein. Similarly, p91 and STAT1 denote the same transcription factor and these terms are used interchangeably herein.

The process of identifying and preparing peptides that can bind and inactivate a specific STAT-family transcription factor is exemplified below for IFNγ and IL-10 systems. Briefly, according to this method, first cytokine receptors that utilize a particular or combination of particular STAT family transcription factors are identified. There are six known members of the STAT family, STAT 1 (p91), STAT 2 (p113), STAT3 (APRF), STAT 4, STAT 5 (MGF) and IL-4 STAT. (Hou et al., *Science* 265:1701–1706, 1994 which is incorporated by reference). Cells having different cytokine receptors are tested using the particular cytokine to stimulate a given cell and a gel shift assay is used with individual STAT antisera used to determine which STAT family transcription factor or factors are used by the particular cell. Next, after a cell is determined to use a particular STAT in its cytokine signal transduction, tyrosine residues are located in the receptor sequence. (For receptor sequences of cytokine-activatable cells see *Guidebook to Cytokines and Their Receptors*, N. Nicola, ed. Oxford University Press, Oxford, U.K. 1994 which is incorporated by reference). The importance of tyrosine residues was determined for IFN-γ by preparing mutant cytokine receptor constructs lacking the tyrosine residues and testing transfected cells for transcription factor activation. Therefore, this additional step would not be necessary for subsequent identification of other STAT-family-member transcription factors. Next, polypeptides are prepared comprising a sequence of approximately 9–12 amino acids that corresponds to the receptor sequence of amino acids containing the tyrosine residue with the modification that the tyrosine residue is phosphorylated. The polypeptide is then aminoterminally biotinylated and tested in the electrophoretic mobility shift assay to determine if the polypeptide inhibits STAT activation.

Signal transduction for IFNγ involves activation of the p91 family of transcription factors also termed STAT1. The terms p91 and STAT1 denote the same transcription factors and are used interchangeably herein.

Although it had previously been shown that IFNγ induced the phosphorylation and activation of a cytoplasmic transcription factor, p91, the relationship between IFNγ, the IFNγ receptor, and the cytoplasmic transcription factor, was not known.

In one embodiment, this invention describes the heretofore unrecognized direct and specific interaction of a member of a family of proteins that exhibit transcriptional activation properties in response to IFNγ with a peptide derived from the IFNγ receptor α chain molecule.

One composition of the present invention comprises a peptide that includes a sequence of 5 amino acids that comprises a phosphorylated tyrosine linked to an aspartate residue, two amino acid residues that can be any amino acid, and a histidine residue, and can be denoted by $Xaa_1$-Asp-$Xaa_2$-$Xaa_3$-His wherein $Xaa_1$ is a phosphorylated tyrosine. This amino acid sequence is identified as SEQ ID NO:1. It has been found that a peptide molecule containing this sequence is capable of directly and specifically binding to the p91 transcription factor family and inhibiting its transcriptional activity in a cell. This 5 amino acid sequence corresponds to the sequence of amino acids 440–444 (Tyr-Asp-Lys-Pro-His, SEQ ID NO:2) of the IFNγ receptor molecule except that the tyrosine residue in the composition of the present invention is phosphorylated. By phosphorylating the tyrosine residue in the amino acid sequence of SEQ ID NO:2, it is possible to cause the specific binding of the phosphorylated peptide with the p91 transcription factor in the cell.

In another embodiment, this invention involves the direct and specific interaction of a member of a family of proteins that exhibit transcriptional activation properties in response to IL-10 with a peptide derived from the IL-10 receptor. It is shown that IL-10 induces the phosphorylation and activation of a cytoplasmic transcription factor, the 92 kD protein, STAT3.

This embodiment includes two compositions of the present invention. One composition comprises a peptide that includes a sequence of 5 amino acids that comprises the sequence denoted by Xaa-Gln-Lys-Gln-Thr wherein Xaa is a phosphorylated tyrosine. This amino acid sequence is identified as SEQ ID NO:20. The other composition comprises the sequence denoted by Xaa-Leu-Lys-Gln-Glu wherein Xaa is a phosphorylated tyrosine. This amino acid sequence is identified as SEQ ID NO:21. It has been found that a peptide molecule containing either of these sequences is capable of directly and specifically binding to the 93 kD, STAT3 transcription factor and inhibiting its transcriptional activity. This 5 amino acid sequence corresponds to the sequence of amino acids 427–431 (Tyr-Gln-Lys-Gln-Thr, SEQ ID NO:22) and 477–481 (Tyr-Leu-Lys-Gln-Glu, SEQ ID NO:23) of the IL-10 receptor molecule except that the tyrosine residues in the composition of the present invention are phosphorylated. By phosphorylating the tyrosine residue in the amino acid sequences of SEQ ID NO:20 and SEQ ID NO:21, it is possible to cause the specific binding of the phosphorylated peptides with the 93 kD, STAT3 transcription factor in the cell.

The novel peptides of the present invention may comprise a longer peptide than SEQ ID NO:1 or SEQ ID NO:20 or SEQ ID NO:21 by having more amino acids added to either of the terminal amino acids so long as the resulting peptide remains capable of binding to the transcription factor. Thus, amino acid sequences can be introduced at either end of the amino acid sequence of SEQ ID NO:1 or SEQ ID NO:20 or SEQ ID NO:21 and be considered within the scope of the present invention. In addition, certain amino acids within SEQ ID NO:1 or SEQ ID NO:20 or SEQ ID NO:21 can be replaced with other amino acids so long as the phosphotyrosine is retained. Preferably, peptides prepared in accordance with this are between five and about thirty amino acids in length. The peptides can be derived from the IFNγ or IL-10 receptor amino acid sequences or can be an unrelated sequence provided that the five amino acid sequence of SEQ ID NO:1 or SEQ ID NO:20 or SEQ ID NO:21 is included in the peptide or is similar to the sequence of SEQ ID NO:1 or SEQ ID NO:20 or SEQ ID NO:21 maintaining that the tyrosine in that amino acid sequence is phosphorylated.

The tyrosine residue in a peptide sequence can be phosphorylated by known methods. Nonhydrolyzable phosphotyrosyl mimetics can also be used in replacement of the phosphotyrosyl residue. (See, for example Burke et al, *Biochemistry* 33:6490–6494, 1994). The peptide also can be produced by standard synthetic procedures such as by "classical" Merrifield method of solid phase peptide synthesis or by using the FMOC strategy on a RAMPS multiple peptide synthesis system (DuPont Co., Wilmington Del.) as described in Caprino and Han (1972 which is incorporated by reference). Other exemplary peptides suitable for use in binding to p91 transcription factors include sequences containing the ninemer Thr-Ser-Phe-Gly-Xaa-Asp-Lys-Pro-His, where Xaa is phosphorylated tyrosine, identified as SEQ ID NO:3, or the dodecamer Thr-Ber-Phe-Gly-Xaa-Asp-Lys-Pro-His-Val-Leu-Val, where Xaa is a phosphorylated tyrosine, identified as SEQ ID NO:4. Exemplary peptides suitable for use in binding to the 93 kD, STAT3 transcription factor include sequences containing the dodecamer Thr-Phe-Gln-Gly-Xaa-Gln-Lys-Gln-Thr-Arg-Arg-Trp-Lys, where Xaa is a phosphorylatedtyrosine, identified as SEQ ID NO:24 and the dodecamer Leu-Ala-Ala-Gly-Xaa-Leu-Lys-Gln-Glu-Ser-Ser-Gln-Gln, where Xaa is a phosphorylated tyrosine, identified as SEQ ID NO:25.

After a suitable peptide has been made, the peptide can be prepared in a pharmaceutically acceptable composition that is capable of delivering the peptide into to a cell. Any known and available means can be used for delivering the peptide into a cell. For example, the peptide may be incorporated with a carrier moiety such as a liposome that is capable of delivering the peptide into the cytosol of a cell. Such methods are well known in the art (for example see Amselem et al., *Chem Phys Lipids* 64:219–237, 1993 which is incorporated by reference). Alternatively, the peptide can be modified to include specific transit peptides that are capable of delivering the peptide into the cytoplasm of a cell or the peptide can be delivered directly into a cell by microinjection.

An effective amount of the peptide must be introduced into the cell so that binding of the transcription factor takes place. It is to be understood that the amount of peptide necessary to be introduced into any particular cell is dependent upon the cell, but can be determined using standard dose/response analysis.

Based on the structural features of the critical amino acid sequence of the peptides of the present invention that permit the binding of the peptide with the transcription factor, one can develop non-peptide derivatives that are capable of binding to the transcription factors. It is believed that at a minimum, non-peptide compositions that would be capable of binding transcription factors would contain a phosphorylated tyrosine-like structure and would be capable of being introduced into a cell.

The techniques for development of peptide mimetics are well known in the art. (See for example, Navia and Peattie, *Trends Pharm Sci* 14:189–195, 1993; Olson et al, *J Med Chem* 36:3039–3049 which are incorporated by reference). Typically this involves identification and characterization of the protein target as well as the protein ligand using X-ray crystallography and nuclear magnetic resonance technology. In the case of IFNγ-activatable p91 transcription factor, the transcription factor has been sequenced and cloned and the ligand sequence as well as the complete sequence for the IFNγ receptor are known. (Schindler et al., *Proc Natl Acad Sci* 89:7836–7839, 1992; Aguet et al. *Cell* 55:273–280, 1988 which are incorporated by reference). Using information learned from the structure of the target protein and ligand, a pharmacophore hypothesis is developed and compounds are made and tested in an assay system. Either electrophoretic mobility shift assays (Igarashi et al. *Mol Cell Biol* 13:1634–1640, 1993 which is incorporated by reference) or an assay system utilizing co-precipitation of ligand and transcription factor can be used.

The peptide ligands of the present invention also can be used to detect non-peptide compositions capable of binding transcription factors. A standard radioligand assay system can be used. (For example, see Bylund and Toews, *Am J Physiol* 265:L421–429, 1993 which is incorporated by reference). This can be done by first preparing a labeled form of the peptide using either $^3$H or $^{125}$I or biotinyation according to standard methods. For example, the Bolton Hunter Reagent can be used (ICN Chemicals, Radioisotope Division, Irvine, Calif.). The composition of transcription factor to which the radioligand binds can be prepared from cytosolic homogenates. A standard ELISA-style plate assay can be used to bind radiolabeled ligand and then recover and measure the amount of bound ligand. (For example see Slack et al. *BioTechniques* 7:1132–1138, 1989; Dower et al, *J Immunol* 142:4314–4320, 1989 which are incorporated by reference). Competitive inhibition of the binding of the radiolabeled peptide ligand to the transcription factor on addition of a test compound can be evaluated by standard methods of analysis. (For example, see Rovati, *Pharmacol Res* 28:277–299, 1993 which is incorporated by reference). Alternatively, a non-radiolabling method can be used to detect competitive displacement of the peptide ligand from the transcription factor. The assays can also be performed by using solid phase peptide and labeled forms of purified, recombinant transcription factor.

The peptides and derivatives of the present invention can be evaluated in animal models that mimic disease processes. Peptides binding to p91 to inhibit IFNγ activity would be expected to show activity where monoclonal antibody to IFNγ was effective including the treating of insulin-dependent (type I) diabetes mellitus, the blocking-allograft rejection, the treating of lupus erythematosus, and in the treating other diseases involving uncontrolled immune response or inflammatory response such as autoimmune and inflammatory diseases.

For example, the non-obese diabetic mouse has been used as an animal model of human insulin-dependent diabetes mellitus. (Debray-Sachs et al. *J Autoimmun* 4:237–248, 1991 which is incorporated by reference). Treatment of these mice with anti-IFNγ monoclonal antibody is known to prevent the induction of the disease by cyclophosphamide as well as the adoptive transfer of diabetes by spleen cells from diabetic mice. The peptides and derivatives thereof that bind and inactivate the p91 transcription factor can be administered to these animals in a pharmaceutically acceptable composition. The glucosuria as well as histopathologic indications of diabetes would be expected to be diminished by such treatment.

The peptide binding the p91 transcription factor to inhibit IFNγ activity would also be expected to block IFNγ dependent allograft rejection. Monoclonal antibodies to IFNγ are known to block the allograft rejection response of CBA/j mice to challenge with tumor cells from BALB/c mice. (Landolfo et al., *Science* 229:176–178, 1985 which is incorporated by reference). Administration of the IFNγ blocking peptides and derivatives thereof in a pharmaceutically acceptable composition would be expected to inhibit the allograft rejection response. Furthermore, the IFNγ inhibiting peptides and derivatives administered with cyclosporine therapy would be expected to prolong cardiac allograft survival in the rat (Didlake et al., *Transplantation* 45:222–223, 1988 which is incorporated by reference).

Inhibition of IFNγ activity by inactivating the p91 transcription factor would also be expected to be effective in treating autoimmune diseases such as the glomerulonephritis of (NZB×NZW)F$_1$ hybrid mice. This disease mimics lupus erythematosus and the administration of monoclonal antibodies to IFNγ is known to produce remission. (Jacob et al. *J Exp Med* 166:798–803, 1987 which is incorporated by reference). Administration of peptides and derivatives of the present invention to bind the p91 transcription factor and inhibit IFNγ activity would be expected to produce remission of the disease.

Inflammatory reaction to bacterial lipopolysaccharide challenge (Schwartzman reaction) is known to be inhibited by anti-IFNγ (Billiau, *Immunol Today* 9:37–40, 1988 which is incorporated by reference). Administration of peptides and derivatives of the present invention to bind the p91 transcription factor and inhibit IFNγ activity would be expected to block this reaction in mice as well as in the diseases this model mimics such as meningococcal-septicaemia-associated shock, allergic Coombs Type III reactions provoked by antigen-antibody complexes and abortion due to Gram-negative septicaemia.

The peptides and derivatives thereof prepared in accordance with the present invention can be used to inhibit the intracellular activation of cytokine-inducible transcription factors in a mammalian cell and thereby provide a useful therapeutic composition for use in the treatment of diseases. Peptides and derivatives thereof that inhibit activation of IFNγ inducible transcription factors are useful in treating insulin-dependent (type I) diabetes mellitus, in blocking allograft rejection, in treating lupus erythematosus, and in treating other diseases defined by an uncontrolled immune response or inflammatory response such as autoimmune and inflammatory diseases. The peptides of the present invention may also be useful in the treatment of cancer by targeting the peptide to cancerous cells.

The following examples further describe the materials and methods used in carrying out the invention and are provided to illustrate the present invention and are not intended to limit the invention in any manner.

EXAMPLE 1

This example illustrates the discovery that IFNγ was capable of inducing tyrosine phosphorylation of its own receptor and that the tyrosine residue at amino acid position 440 of the IFNγ receptor was a specific phosphorylation substrate.

For these experiments, Colo-205, a human adenocarcinoma cell line obtained from the ATCC, was used because it was known to express a high number of IFNγ receptors (10,000 receptors/cell) and has been well characterized with regard to both biologic responsiveness to IFNγ and IFNγ receptor serine/threonine phosphorylation (Hershey and Schreiber, 1989; Hershey et al., 1990 both of which are incorporated by reference). Colo-205 cells (5–10×10$^7$) were resuspended in one ml of PBS-10% FCS and were then incubated at 37° C., either in the presence or absence of rHuIFNγ (10,000 IRU). Purified recombinant human IFNγ was provided by Dr. Susan Kramer of Genentech, Inc. (South San Francisco, Calif.). The rHuIFNγ used displayed specific antiviral activities of 3.8×10$^7$ IRU/mg. Purified rHuIFNγ was radioiodinated, using Bolton Hunter reagent (ICN Chemicals, Radioisotope Division, Irvine, Calif.) to specific activities of 6.5–17.8 µCi/µg as described in Celada et al. (*J Clin Invest* 76:2196–2205, 1985 which is incorporated by reference). The reaction was stopped by adding 4 mls of ice-cold PBS. Cells were pelleted, washed once in ice-cold PBS, and then lysed in one ml of lysis buffer (25 mM Tris-HCl (pH 8.0), 1% NP-40, 150 mM NaCl, 1 mM sodium orthovanadate, 10 mM NaF, 1 mM PMSF, 5mM iodoacetamide, 10 mg/ml leupeptin and aprotinin). Solubilized cells were centrifuged at 15,000×g to remove cell nuclei and the supernatants were then incubated with 10 μg of GIR-94 for 30 minutes at 4° C. Protein G sepharose was added to the reaction mixture and the incubation continued for an additional 30 minutes. The beads were pelleted by centrifugation (10,000×g, for 3 minutes at 4° C.) and then washed 3 times with lysis buffer containing 1% SDS, 0.5% deoxycholate and 1% BSA and 2 times with PBS containing 1 mM sodium orthovanadate. Beads were resuspended in 50 μl of 2×laemmli buffer containing 180mM β-mercaptoethanol, heated to 65° C. for 5 minutes, and pelleted by centrifugation. The supernatants were removed and one third of each sample used for western blotting with GIR-94 (anti-IFNγ receptor) while the remaining two thirds used for western blotting with murine IgG$_{2b}$ antiphosphotyrosine monoclonal antibody, 4G10, obtained from UBI (Lake Placid, N.Y.). Samples were loaded and electrophoresed on 4%–15% SDS-polyacrylemide gels (Biorad, Richmond, Calif.). Fractionated proteins were then transferred electrophoretically to nitrocellulose. Nitrocellulose membranes were blocked 1–18 hours at 4° C. in PBS containing 5% non-fat dry milk. The membranes were then washed with PBS-tween (0.05% tween-20) and incubated for one hour with either biotinylated GIR-94 or 4G10 (1 mg/ml). The membranes were then washed and incubated for 20 minutes in streptavidin-horseradish peroxidase and subsequently developed by chemiluminescence using Amersham's (Arlington Heights, Ill.) ECL western blotting system. The specificity of the phosphotyrosine antibody was confirmed by the ability of O-phospho-DL-tyrosine but not O-phospho-L-serine or O-phospho-L-threonine to block 4G10 from binding to the nitrocellulose bound receptor.

To determine the amount of receptor precipitated at each time point, aliquots from each immunoprecipitate were subjected to western blot analysis using a monoclonal antibody (GIR-94, a murine antibody IgG$_{2b}$) that is specific for the human IFNγ receptor extracellular domain. In the absence of added IFNγ, no tyrosine phosphorylated receptor was detected (FIG. 1, lane 1). However, following addition of IFNγ, a rapid and reversible phosphorylation of the receptor was observed. IFNγ receptor α chain phosphorylation reached maximum levels between 15 seconds and 1 minute after IFNγ addition (FIG. 1, lanes 2 and 3, respectively), remained at plateau levels through 5 minutes (lane 4), was significantly reduced at 15 minutes (lane 5) and approached background levels by 30 minutes (lane 6). IFNγ dependent tyrosine phosphorylation of the IFNγ receptor α chain was inhibited by pretreatment of the cells with herbimycin A (1 mM). Interestingly, this treatment also blocked IFNγ dependent MHC class II induction on these cells. The specificity of the 4G10 western blotting was confirmed by three criteria. First, detection of the tyrosine-phosphorylated receptor α chain was blocked if the 4G10 mAb was pre-incubated with phosphotyrosine but not with phosphoserine or phosphothreonine. Second, the same band was detected using another phosphotyrosine specific mAb (PY20). Third, the phosphorylated IFNγ receptor α chain could also be detected when 4G10 was used to immunoprecipitate phosphoproteins from lysates of IFNγ treated cells and western blot analysis performed using the IFNγ receptor specific GIR-94 monoclonal antibody.

These results thus demonstrate that IFNγ induced tyrosine phosphorylation of the IFNγ receptor α chain is an extremely rapid process and establishes that tyrosine phosphorylation of the IFNγ receptor α chain is the earliest response yet observed of cells to IFNγ.

To further characterize the tyrosine phosphorylation of the IFNα receptor and to partially validate its biologic significance, concomitant dose-response phosphorylation and MHC class II induction analyses were performed. Colo-205 cells (1×10$^8$ cells/ml) were stimulated for 5 minutes with the indicated concentrations of rHuIFNγ as shown in FIG. 2. Cells were lysed and the IFNγ receptor immunoprecipitated, subjected to SDS-PAGE and electrophoretically transferred to nitrocellulose membranes as described above. Membranes were blotted with the mAb 4G10 (anti-phosphotyrosine) as described. Colo-205 cells (1×10$^8$ cells/ml) were also stimulated for 5 minutes with the indicated concentrations of rHuIFNγ, washed, and incubated an additional 48 hours in the absence of rHuIFNγ. MHC class II expression was quantitated by flow cytometric analysis.

Figure 2A:
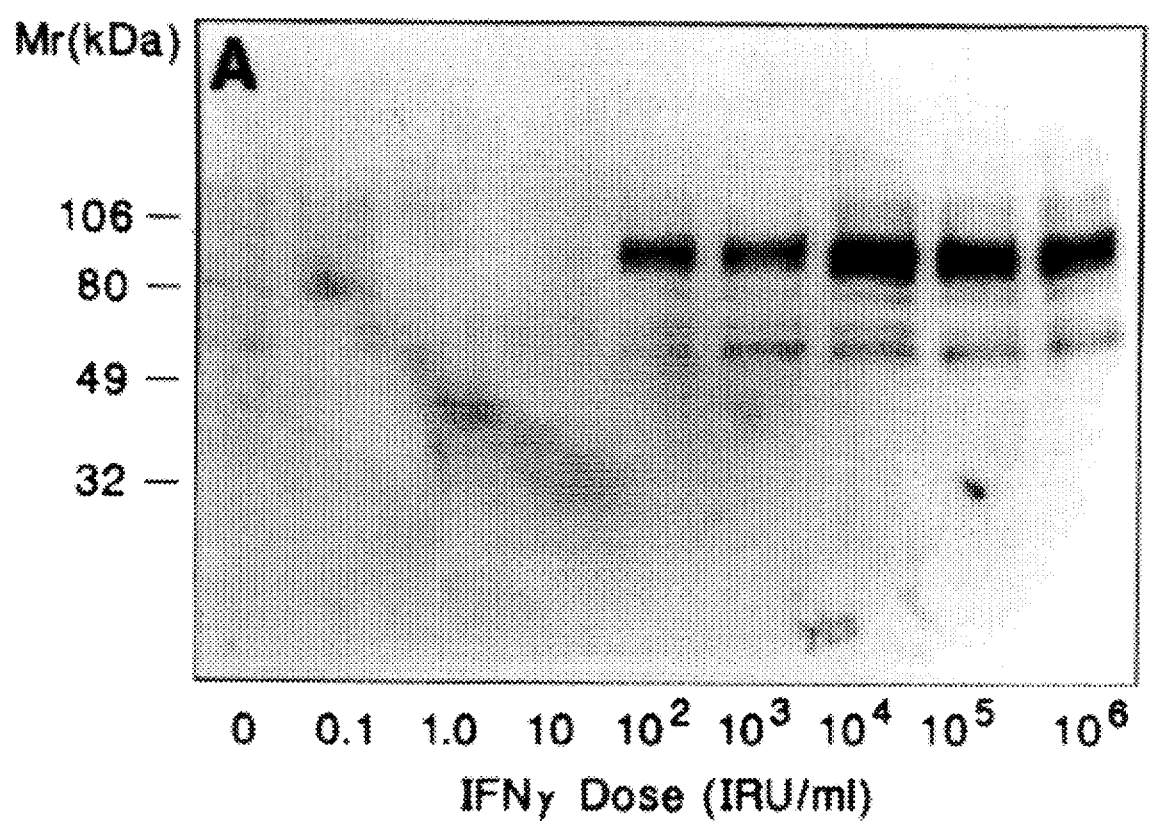
FIG. 2A is a western blot illustrating the dose response of receptor phosphorylation in response to IFNγ doses.
Figure 2B:
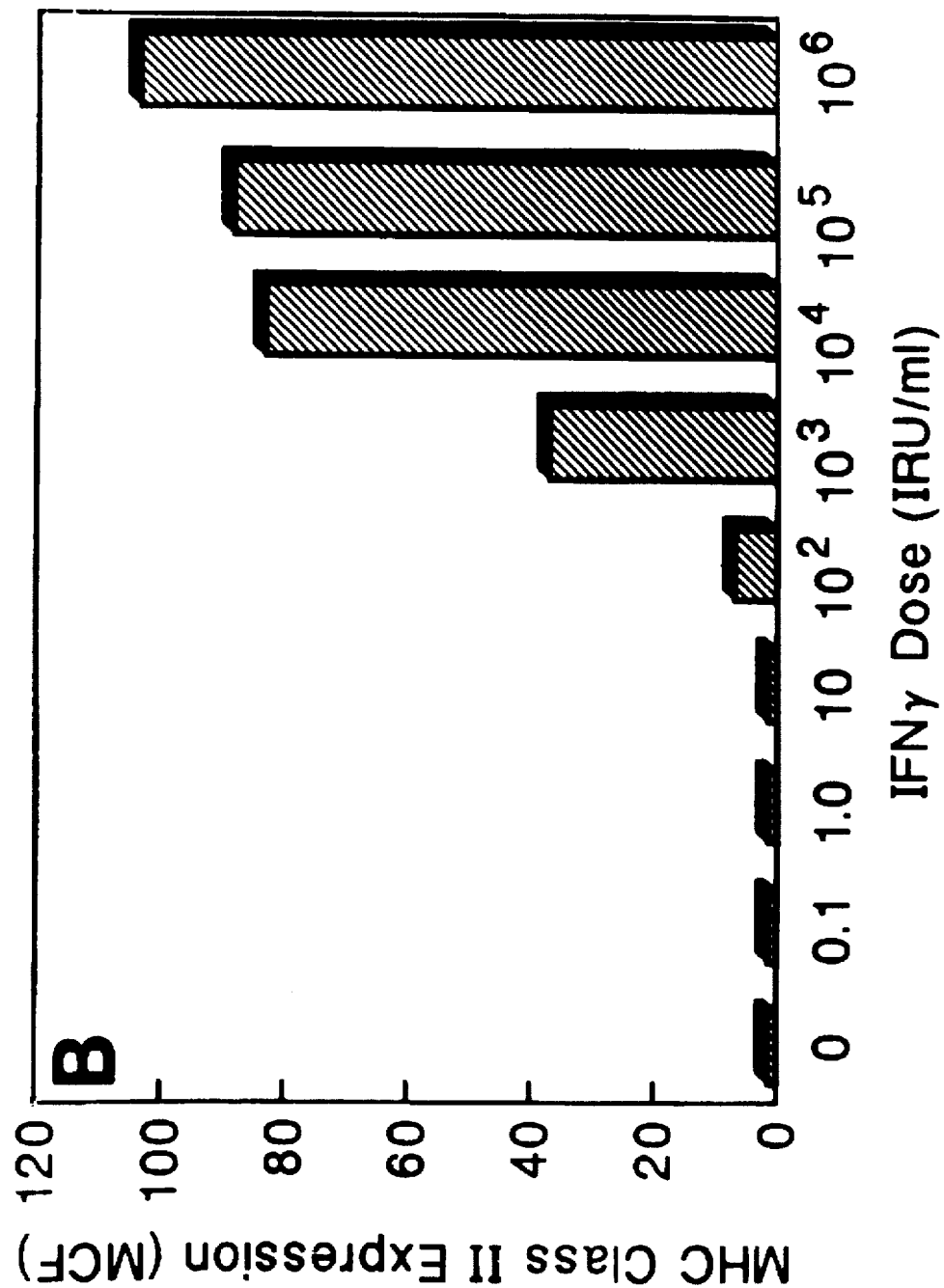
FIG. 2B is a graphical representation of the kinetics of MHC class II induction analyses in response to IFNγ doses.

IFNγ receptor tyrosine phosphorylation was detected when 10$^8$ Colo-205 were treated for 5 minutes with 100 IRU/ml of IFNγ and reached maximal levels at IFNγ doses of 10,000 IRU/ml (FIG. 2A). A similar profile was obtained for the induction of an IFNγ biologic response in these cells (MHC class II induction) when Colo-205 were exposed to identical doses of IFNγ for 5 minutes, washed and then placed back in culture for 48 hours to allow time for the biologic response to develop (FIG. 2B). Thus, the amount of IFNγ required to induce IFNγ receptor tyrosine phosphorylation parallels that required to induce biologic responses.

EXAMPLE 2

This example illustrates the requirement of the presence of the species-specific receptor β chain for IFNγ dependent tyrosine phosphorylation of the IFNγ receptor chain.

Figure 3A:
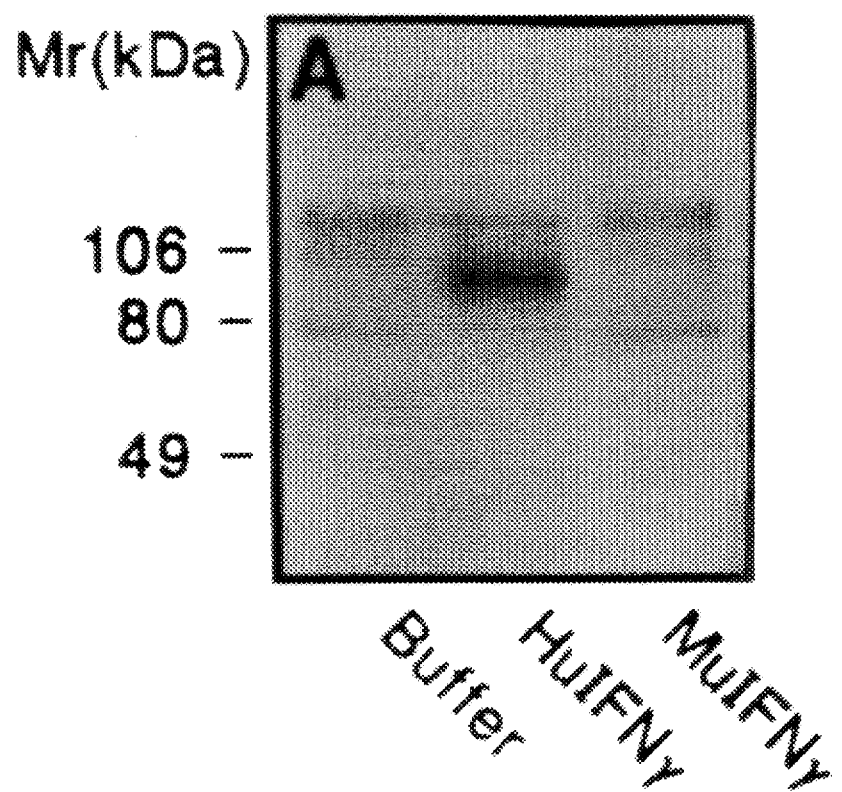
FIG. 3 is series of western blots illustrating that the IFNγ receptor c chain requires the presence of the species-specific receptor β chain for IFNγ dependent tyrosine phosphorylation.
Figure 3B:
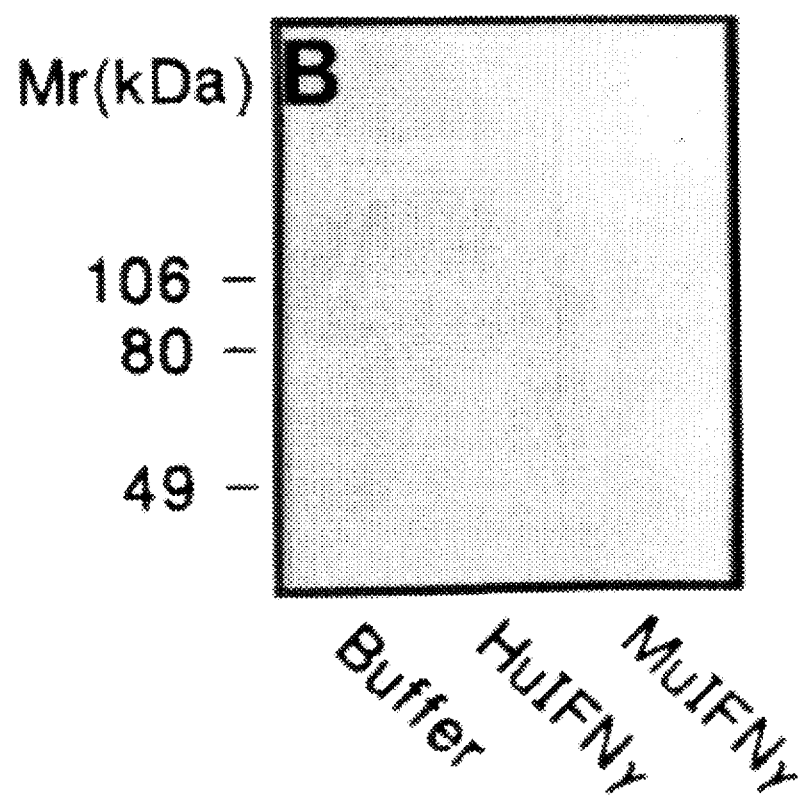
Figure 3C:
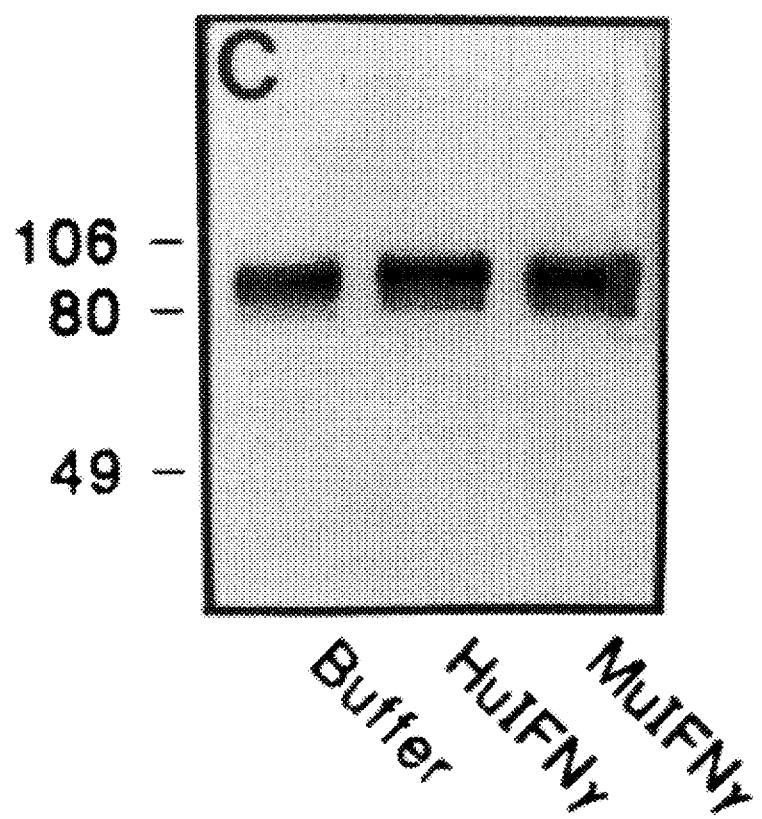
Figure 3D:
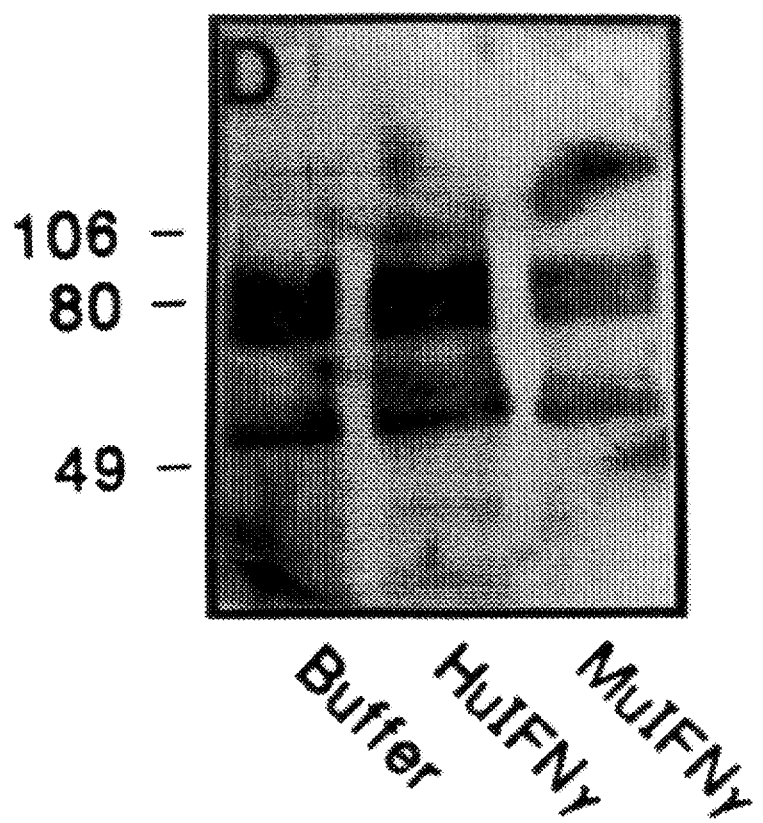

Cellular responsiveness to IFNγ requires the presence of both species matched receptor α and β polypeptide chains (Jung et al., *Proc Natl Acad Sci* 84:4151–4155, 1987; Jung et al., *J Biol Chem* 265:1827–1830, 1990; Fischer et al., *Cytokine* 2:157–161, 1990; Farrar et al., *J Biol Chem* 266:19626–19635, 1991; Gibbs et al., *Mol Cell Biol* 11:5860–5866, 1991; Hemmi et al., *Proc Natl Acad Sci* 89:2737–2741, 1992 which are incorporated by reference). To determine whether a similar requirement is shown for IFNγ induced IFNγ receptor tyrosine phosphorylation, a Colo-205 cell line that stably expressed the murine IFNγ receptor β chain designated M-Colo.22 (Hershey et al., *J Biol Chem* 165:17868–17875, 1990 which is incorporated by reference) was utilized. On these cells, the transfected murine receptor α chain binds and processes murine IFNγ in a normal manner but is unable to support biologic responses (such as MHC class II induction) to murine IFNγ. M-Colo.22 cells were incubated with buffer (lane 1 and 4), rHuIFNγ (10,000 IRU/ml) (lane 2 and 5), or rMuIFNγ (10,000 IRU/ml) (lane 3 and 6) for 5 minutes at 37° C. Cells were lysed and the human IFNγ receptors (Panel A and C of FIG. 3) or murine IFNγ receptors (Panel B and D of FIG. 3) were immunoprecipitated using the mAb GIR-94 or polyvalent goat anti-murine IFNγ receptor immune sera, respectively. Immunoprecipitates were subjected to SDS-PAGE and electrophoretically transferred to nitrocellulose membranes as previously described. Human IFNγ receptor (Panel A and C of FIG. 3) and murine IFNγ receptor (Panel B and D of FIG. 3) immunoprecipitates were blotted with the mAbs 4G10 (anti-phosphotyrosine) (Panel A and B), GIR-208 (anti-human IFNγ receptor) (Panel C), or GR-20 (anti-murine IFNγ receptor) (Panel D). As shown in FIG. 3, treatment of M-Colo.22 for 5 minutes at 37° C. with 10,000 IRU/ml of human IFNγ resulted in tyrosine phosphorylation of the endogenous human IFNγ receptor (FIG. 3A, lane 2)

but not the transfected murine IFNγ receptor (FIG. 3B, lane 5). Stimulation of cells with murine IFNγ did not result in tyrosine phosphorylation of either the human or murine IFNγ receptors (FIG. 3A and 3B, lanes 3 and 6, respectively). The cell line expressed equivalent levels of both the human and murine receptor α chains as documented by immunoprecipitation and western blot analyses using monoclonal antibodies specific for each species of receptor α chain (FIG. 3, panels C and D). These results demonstrate that the species specific IFNα receptor β chain is required for the IFNγ induced tyrosine phosphorylation of the IFNγ receptor α chain.

EXAMPLE 3

This example is provided to illustrate that the functionally critical carboxy terminal region of the IFNγ receptor α chain is not required for tyrosine kinase activation but is a target for tyrosine phosphorylation.

The complete nucleotide and amino acid sequence of the IFNγ receptor α chain is known and described in Aguet et al. (*Cell* 55:273–280, 1988 which is incorporated by reference), the entirety of which is hereby incorporated by reference hereto. Although there are five tyrosine residues within the intracellular domain of the IFNγ receptor α chain (Aguet et al., supra), only one (Y440) is functionally important (Farrar et al., supra). Therefore, the issue of whether Y440 is required for tyrosine kinase activation or is a substrate for and was isolated. A second PCR reaction was conducted in a similar manner utilizing oligonucleotide primer #491066 which has the sequence 5'-GTTTATCAAAACCAAAGGAGG-3, (SEQ ID NO:6) and an IFNγ receptor α chain upstream primer sequence that is 5' to Y440 to introduce the tyrosine to phenylalanine mutation into the complementary DNA strand. The resulting PCR cDNA product contained the tyrosine to phenylalanine mutation and was isolated. The two PCR products were then permitted to anneal in the area of complementarity and a third PCR reaction was conducted using other oligonucleotides corresponding to the 5' and 3' ends of the IFNγ receptor α chain to generate a full length mutant sequence. This PCR product was then digested with SacI end ClaI which provided a fragment containing the F440 mutation and purified. This fragment was introduced into pBluescript which contained the native IFNγ receptor sequence, but which had been cleaved with ClaI and SacI to remove the region therebetween which contained Y440. The resulting mutant IFNγ receptor was cloned into pSFFV for expression and subsequent transfection. Using a similar PCR procedure, the mutant designated 4XYF was produced by sequential introduction of tyrosine to phenylalanine mutations at amino acid positions 287, 294, 380 and 462 using the following oligonucleotide PCR primers, respectively, to introduce the desired mutation:

---

For YF287, 294:
Primer #000001
5' TGTATCACTCATCACGTCATTCCAGCCATTTTCGTTAGAAAAGG 3' (SEQ ID NO:7) and
Primer #000002
5' ATGACGTGATGAGTGATACAAATTTTGATTCAGG 3' (SEQ ID NO:8)
For YF380:
Primer #000003 5' CGCTTTGAACTCGTTTCAATACAG 3' (SEQ ID NO:9)
and
Primer #000004 5' CTGGAGTGAAACGAGTTCAAAGCGATG 3' SEQ ID NO:10)
For YF462:
Primer #000005
5' CCATCGATGTCATGAAAATTCTTTGGAATCTTCTGTTGGTCTAAAACCAATC3' (SEQ ID NO:11)

--- the activated kinase was analyzed. This issue was addressed using a family of human chromosome 21 containing murine fibroblasts (SCCl6-5 which is a murine fibroblast cell line that contains a single copy of human chromosome 21 as described in Janssen et al. (*Cyto &:*411-417, 1986 which is incorporated by reference) and WA-17 which is a murine L cell line that contains three copies of human chromosome 21 as described in Raziuddin et al., (*Proc Natl Acad Sci* 81:5504–5508, 1984 which is incorporated by reference) that were transfected to stably express either the wild type human IFNγ receptor α chain, a human receptor α chain containing a point mutation in which Y440 was replaced by phenylalanine (referred to as YF440), or a third α chain mutant in which all the intracellular domain tyrosine residues except Y440 were replaced by phenylalanine (designated 4XYF). The mutant IFNγ receptor α chains designated YF440 and 4XYF were produced by the PCR method. The tyrosine to phenylalanine mutation in YF440 was introduced in one strand of the native IFNγ receptor α chain by PCR utilizing primer #482019 which has the sequence 5' CCTCCTTTGGTTTTGATAAAC-3' (SEQ ID NO: 5) and an IFNγ receptor α chain downstream oligonucleotide that is 3' to Y440. The resulting PCR cDNA product contained the tyrosine to phenylalanine mutation Cells were transfected with all three constructs using the calcium phosphate precipitation method as described in Farrar et al. (1992). Cells transfected with all three constructs expressed comparable levels of each receptor form and bound and internalized IFNγ in a manner that was indistinguishable from native receptors on normal human cells. All three cell lines responded to homologous murine IFNγ indicating that the general class I MHC induction pathway was intact. Furthermore, the cell lines responded to IFNα2a indicating that they still contained human chromosome 21 and hence maintained expression of the human receptor β chain. However, only the cell lines that expressed wild type receptor α chain and the 4XYF mutant responded to human IFNγ while the YF440 mutant expressing cell line did not. This observation again reinforced the earlier finding that Y440 was the only functionally critical tyrosine residue within the receptor α chain's intracellular domain.

The three transfected cell lines were then tested for their capacity to phosphorylate IFNγ receptor tyrosine residues in response to human IFNγ. For each cell line, human receptor α chain phosphorylation in buffer- and IFNγ-treated cells was studied by western blotting using 4G10 and human IFNγ receptor α chain expression confirmed by western blotting with GIR-94. Cells were stimulated with IFN 10,000 units/ml for 30 seconds, lysed, human IFNγ receptors immunoprecipitated, immunoprecipitates were subjected to SDS-PAGE, electrotransferred to nitrocellulose, and immunoblotted with GIR-94 or 4G10.

Figure 4:
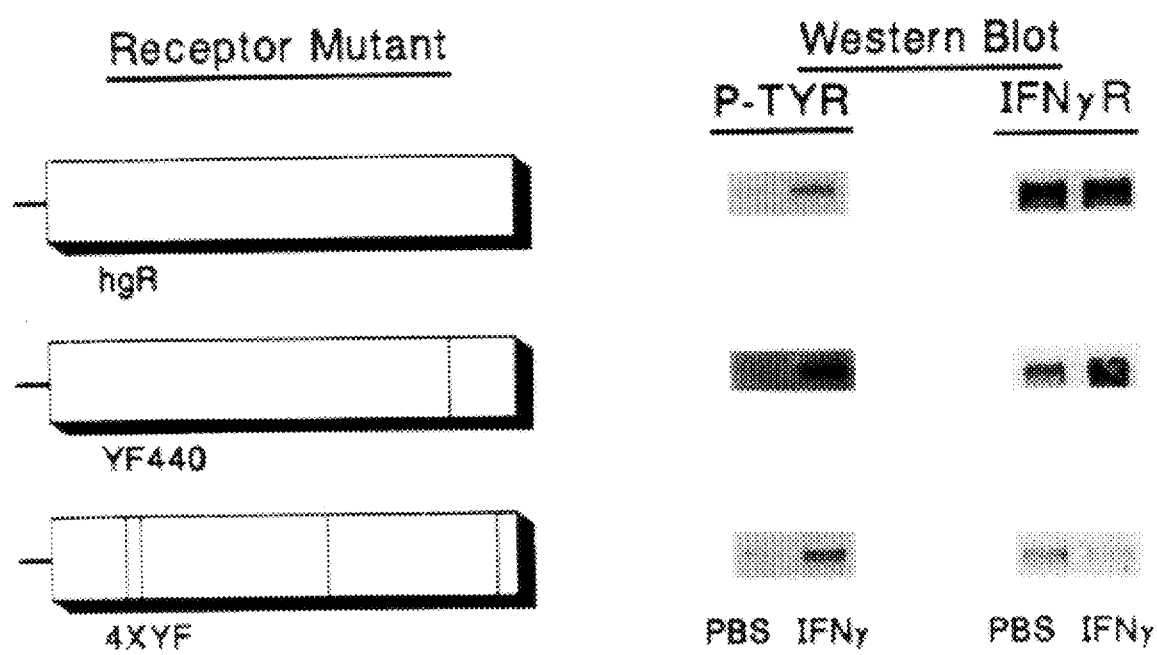
FIG. 4 is a graphical illustration and the corresponding western blot results of WA.17 expressing the wildtype human IFNγ receptor, WA.17 expressing the biologically inactive YF440 mutant IFNγ receptor, and SCC.16 expressing the biologically active IFNγ receptor containing the mutations YF287, YF294, YF380, YF462.

The cell line expressing wild type human IFNγ receptor α chain showed an IFNγ dependent receptor tyrosine phosphorylation response (FIG. 4, top panel). This result documented that IFNγ dependent IFNγ receptor tyrosine phosphorylation could be detected in transfected human chromosome 21 containing murine fibroblasts just as described above for authentic human cells. Interestingly, stimulation of cells expressing the YF440 mutant with human IFNγ also resulted in human receptor α chain tyrosine phosphorylation (FIG. 4, middle panel). This result indicated that either Y440 was not the target of the IFNγ inducible tyrosine kinase activity or that multiple tyrosine residues were phosphorylated following stimulation with ligand. This issue was resolved by the finding that the cell line that expressed the 4XYF mutant that contained only the single functionally important Y440 residue was indeed phosphorylated in response to IFNγ (FIG. 4, bottom panel). These results thus demonstrate that whereas the functionally critical Y440 residue is not required for tyrosine kinase activation, it is nevertheless a target for the activated enzyme.

EXAMPLE 4

This example is provided to illustrate that the phosphorylation of Y440 is required for IFNγ receptor signal transduction and that a phosphorylated IFNγ receptor derived peptide can inhibit the generation of active p91 transcription factor activity.

For this example, the finding that the latent IFNγ inducible transcription factor, p91, can be activated by IFNγ in a cell free system (Igarashi et al., *Mol Cell Biol* 13:1634–1640, 1993 which is incorporated by reference) was utilized to determine the biologic significance of the IFNγ induced tyrosine phosphorylation of the Y440 residue in the IFNγ receptor molecule. Colo-205 homogenates were stimulated with 1900 IRU of human IFNγ and p91 activation monitored using an electrophoretic mobility gel shift assay (EMSA) that employed a $^{32}$P-labeled 18 bp probe derived from the FcγR I gene promoter (Pearse et al., *Proc Natl Acad Sci* 90:4314–4318, 1993 which is incorporated by reference). The EMSAs were carried out essentially as described (Igarashi et al., supra). The oligonucleotide probe was based on the 3' 18 base pairs of the Gamma Response Region (GRR) of the FcγRI gene (Pearse et al., *Proc Natl Acad Sci* 90:4314–4318, 1993 which is incorporated by reference). Top strand: 5'-ATGTATTTCCCAGAAA-3' (SEQ ID NO: 12); Bottom strand: 5'-CTTTTCTGGGAAATA-3' (SEQ ID NO:13). The double stranded oligonucleotide was labeled by filling in the overhanging ends with dATP α $^{32}$P using the klenow large fragment (Boehringer Mannheim, Indianapolis, Ind.). Assays were performed using 5 μg of extract and 25,000 cpm (approximately 1 ng) of the double stranded $^{32}$P labeled GRR probe incubated in 10 mM Tris-HCl (pH7.5), 100 mM KCl, 5 mM MgCl$_2$, 1 mM DTT, 10% glycerol and 4 μg poly(dIdC)(dIdC) (Pharmacia) for 20 minutes at room temperature. The reactions were then electrophoresed through a 6% polyacrylamide gel in 0.25×TBE for 3 hours at 150 V. Gels were dried and subsequently analyzed by autoradiography. Supershifts were performed using antisera to the C-terminus of human p91 (Schindler et al., *Proc Natl Acad Sci* 89:7836–7839, 1992 which is incorporated by reference) at a dilution of 1:100. Specificity of interactions were determined by the addition of 350 ng of the unlabeled GRR probe or 560 ng of the unlabeled 41 base pair double stranded oligonucleotide containing the ISRE of ISG15 (5'-GATCCATGCCTCGGGA-AAGGGAAACCGAAACTGAAGCCAC-3' SEQ ID NO: 14) (David and Larner, *Science* 257:813–815, 1992 which is incorporated by reference).

Colo-205 homogenates were prepared essentially as previously described (Igarashi et al., supra). Briefly, 2×10$_8$ Colo-205 cells were washed in PBS and resuspended in 1 ml of reaction buffer containing 100 mM Hepes (pH 7.4), 20 mM MgCl$_2$, 100 mM NaCl, 200 μM ascorbic acid, 4 mM ATP, 2 mM EGTA, 1 mM PMSF, 10 μg/ml leupeptin and aprotinin. Cells were disrupted in a steel dounce until no intact cells remained. Colo-205 homogenates were diluted to 6.5 mg/ml in reaction buffer and 50 μl aliquots were incubated at 4° C. for 1 hour either in the absence or presence of 5 μl of specific peptides diluted in water. After the preincubation period with peptide, homogenates were incubated for 5 minutes at 37° C. with 1900 IRU of rHuIFNγ added in 5 μl of reaction buffer. The reactions were stopped by the addition of 0.45 ml of stop buffer consisting of 20 mM Hepes (pH 7.4), 1 mM MgCl$_2$, 10 mM KCl, 20% glycerol, 500 μM DTT, 0.1% NP-40, 1 mM PMSF, 10 μg/ml leupeptin and aprotinin. Homogenates were vortexed for 5 seconds and nuclei pelleted by centrifugation at 16,000×g for 5 minutes. The supernatant was then assayed for activation of p91 by electrophoretic mobility shift assay (EMSA). The results of the EMSA are shown in FIG. 5 and the material introduced into the respective lanes as follows:lane 1-Minus IFNγ, lane 2-Plus IFNγ, lane 3-unlabeled GRR, lane 4-unlabeled ISRE, lane 5-Plus Rabbit anti-p91, lane 6-Plus Normal Rabbit Serum, lane 7-83 μM TSFGYDKPH (Thr-Ser-Phe-Gly-Tyr-Asp-Lys-Pro-His, SEQ ID NO:15), lane 8-83 μM TSFGY-PO4DKPH (SEQ ID NO:3), lane 9-17 μM TSFGY-PO4DKPH (SEQ ID NO:3), lane 10-3 μM TSFGY-PO4DKPH (SEQ ID NO:3), lane 11-0.7 μM TSFGY-PO4DKPH (SEQ ID NO:3), lane 12-0.1 μM TSFGY-PO4DKPH (SEQ ID NO:3), lane 13-83 μM TSFGY-PO4AKPA (Thr-Ser-Phe-Gly-Xaa-Ala-Lys-Pro-Ala, where Xaa is phosporylated tyrosine, SEQ ID NO:16), lane 14-83 μM SLIGY-PO4RPTEDSK (Ser-Leu-Ile-Gly-Xaa-Arg-Pro-Thr-Glu-Asp-Ser-Lys, where Xaa is phosphorylated tyrosine, SEQ ID NO:17).

Figure 5:
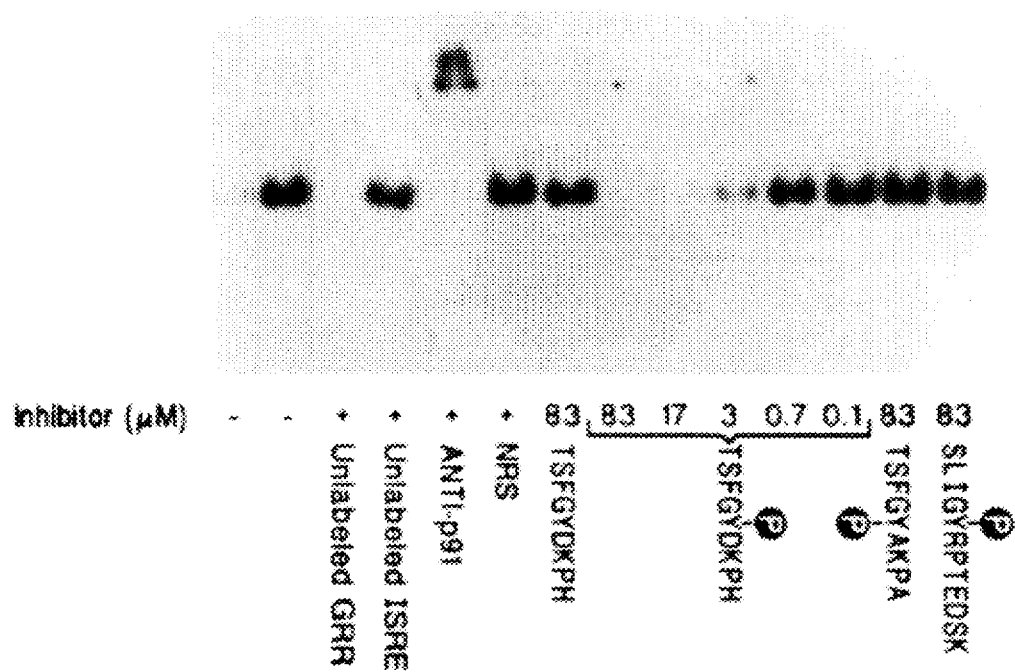
FIG. 5 is a photograph of the results of an electrophoretic mobility shift assay (using SEQ ID NOS:3 and 15–17) identifying that the peptide containing the amino acid sequence of SEQ ID NO:1 with phosphorylated tyrosine blocks the association or activation of the transcription factor p91 with the $^{32}$P labeled oligonucleotide probe.

In the absence of IFNγ, no activated p91 was observed (FIG. 5, Lane 1). In contrast, addition of human IFNγ to the homogenate resulted in the generation of a prominent retarded band (Lane 2). The specificity of the retardation was confirmed by demonstrating that the unlabeled oligonucleotide probe inhibited the formation of the band (Lane 3) while an unlabeled oligonucleotide probe corresponding to the ISRE of ISG15 (David and Larner, supra) did not (Lane 4). The presence of p91 in the gel shift complex was demonstrated using a rabbit antiserum specific for the carboxy terminal portion of human p91 (Schindler et al., supra). Whereas anti-p91 serum effected a supershift of the transcription factor complex when added to the reaction mixture following addition of labeled probe (Lane 5), normal rabbit serum was without effect (Lane 6). These results thus validate the EMSA system and establish that p91 can be activated byligand in homogenates of Colo-205.

To explore the role of Y440 in p91 activation, a series of 9- and 12-amino acid peptides based on sequences from the IFNγ receptor intracellular domain were generated. The peptides: TSFGYDKPH (SEQ ID NO:15), TSFGY-PO$_4$DKPH (SEQ ID NO:3), TSFGY-PO$_4$AKPA (SEQ ID NO:16), SLIGY-PO$_4$RPTEDSK (SEQ ID NO:17), Biotin-TSFGYDKPHVLV (Thr-Ser-Phe-Gly-Tyr-Asp-Lys-Pro-His-Val-Leu-Val, SEQ ID NO:18), Biotin-TSFGY-PO$_4$DKPHVLV (SEQ ID NO:4), Biotin-TSFGY-PO$_4$AKPAVLV (Thr-Ser-Phe-Gly-Xaa-Ala-Lys-Pro-Ala-Val-Leu-Val, where Xaa is phosphorylated tyrosine, SEQ ID NO:19), Biotin-SLIGYPO$_4$RPTEDSK (SEQ ID NO:17) were synthesized manually using the FMOC strategy on a RaMPS™ multiple peptide synthesis system (DuPont Co., Wilmington, Del.) (Caprino and Han, *J Org Chem* 37:3404, 1972 which is incorporated by reference). After addition of phosphotyrosine residues, 35% piperidine/DMF was used to remove the FMOC groups. For the dodecapeptides, biotin groups were added to the amino terminus of the peptides. Briefly, a five fold molar excess of biotinamidocaproate N-hydroxysuccinimide ester was suspended in 3 ml DMSO containing 1% N-methylmorpholine and added to the cartridge containing resin-linked peptide after the final FMOC removal. The slurry was rocked 2 hours, washed 3× in DMF, 3× in MeOH and then an Isatin test was performed to monitor completion of coupling. All peptides, phosphorylated and non-phosphorylated, were cleaved and deprotected according essentially to the protocol of E. A. Kitas et al. (*Helv Chim Acta* 74:1314–1329, 1993 which is incorporated by reference). The resin-linked peptides were treated with 5 ml of 12.9% bromotrimethylsilane, 11.8% thioanisol, 75% trifluoroacetic acid (TFA), and 0.8% m-cresol for 16 hours at 4° C. Peptides were precipitated with tert-butyl methyl ether, redissolved in TFA, and subsequently precipitated and washed 5× with ether, resuspended in water, and lyophilized. Analytical reverse phase HPLC was performed and a single major peak was observed for each peptide. Electrospray mass spectrometry was performed on unfractionated peptides and a single moiety was detected with the predicted molecular mass for each of the peptides. Amino acid composition was verified and molarity calculated using a Beckman 6300 amino acid analyzer.

The peptides were preincubated with Colo-205 homogenates 30–60 minutes before addition of human IFNγ in the EMSA. Pretreatment with a peptide corresponding to residues 436–444 of the human IFNγ receptor α chain (TSFGYDKPH, SEQ ID NO:15) had no effect on p91 activation even when used at a final concentration of 83 µM (FIG. 5, Lane 7). In contrast, pretreatment with a phosphotyrosine containing nonapeptide with the same sequence blocked the activation of p91 in a dose dependent manner (FIG. 5, Lanes 8–12). Formation of an activated p91-labeled probe complex was completely inhibited at phosphopeptide inputs of 83 and 15 µM and 61% inhibited at phosphopeptide concentrations of 3 µM. Lower concentrations of the phosphorylated ninemer (0.7 and 0.1 µM) were not inhibitory. The specificity of the inhibition was confirmed using two additional phosphopeptides. First, no inhibition was noted when a mutated 436–444 phosphopeptide was used in which the functionally critical D441 and H444 residues were changed to alanine (Lane 13). Second, no inhibition was noted when a phosphorylated 12 amino acid peptide was used that was based on an IFNγ receptor α chain intracellular domain sequence (residues 458–469) that contains a functionally unimportant tyrosine residue (Y462) (Lane 14). These results thus suggest that the Y440 based phosphopeptide blocks the association of the IFNγ receptor with specific signaling effector molecules and thereby suggests that phosphorylation of Y440 is a critical event in IFNγ signal transduction.

EXAMPLE 5

This example is provided to illustrate that p91 interacts directly with a phosphorylated tyrosine containing five amino acid sequence comprising SEQ ID NO:1.

Different biotinylated 12 amino acid peptides that contained either tyrosine or phosphotyrosine were incubated with Colo-205 homogenates and examined whether p91 could be coprecipitated with biotinylated peptide using Steptavidin-Agarose. Homogenates from 4×10$^8$ Colo-205 cells were diluted to 15 mg/ml with reaction buffer. 0.5 ml aliquots (approximately 2.5×10$^7$ cell equivalents) were incubated either in the presence of or absence of 23000 IRU of IFNγ for 5 minutes at 37° C. Reactions were stopped by addition of 2.5 ml of stop buffer supplemented with 1 mM sodium orthovanadate and 1 mM EDTA, vortexed 5 seconds and centrifuged 5 minutes at 13,000 rpm. The supernatants were then incubated with the various biotinylated peptides at a final concentration of 2 µM at 4° C. for 1.5 hours. 175 µl of streptavidin-sepharose (Pierce, Rockford, Ill.) was then added and the incubation continued for an additional 1.5 hours. The sepharose was pelleted and washed 5× with 20 mM Hepes (pH 7.4), 150 mM NaCl, 0.5% NP-40, 5% glycerol, 1 mM MgCl$_2$, 500 µM DTT, 1 mM PMSF, 10 µg/ml leupeptin and aprotinin, 1 mM iodoacetamide, 1 mM EDTA, and 1 mM sodium orthovanadate. 40 µl of 2×laemmli buffer was added and samples placed at 75° C. for 5 minutes then electrophoresed on 4–15% SDS-polyacrylamide gels (Biorad). After transfer to nitrocellulose, membranes were blocked in 2.5% non-fat dry milk in 10 mM Tris-HCl (pH 8.0), 150 mM NaCl, 0.05% tween-20. Membranes were washed in the above described buffer without non-fat dry milk and then incubated with a 1:5500 dilution of rabbit antisera directed against the C-terminus of human p91. Membranes were then incubated with a 1:7500 dilution of peroxidase-congugated goat anti-rabbit IgG (United STATes Biochemicals) and detected using ECL (Amersham).

Figure 6A:
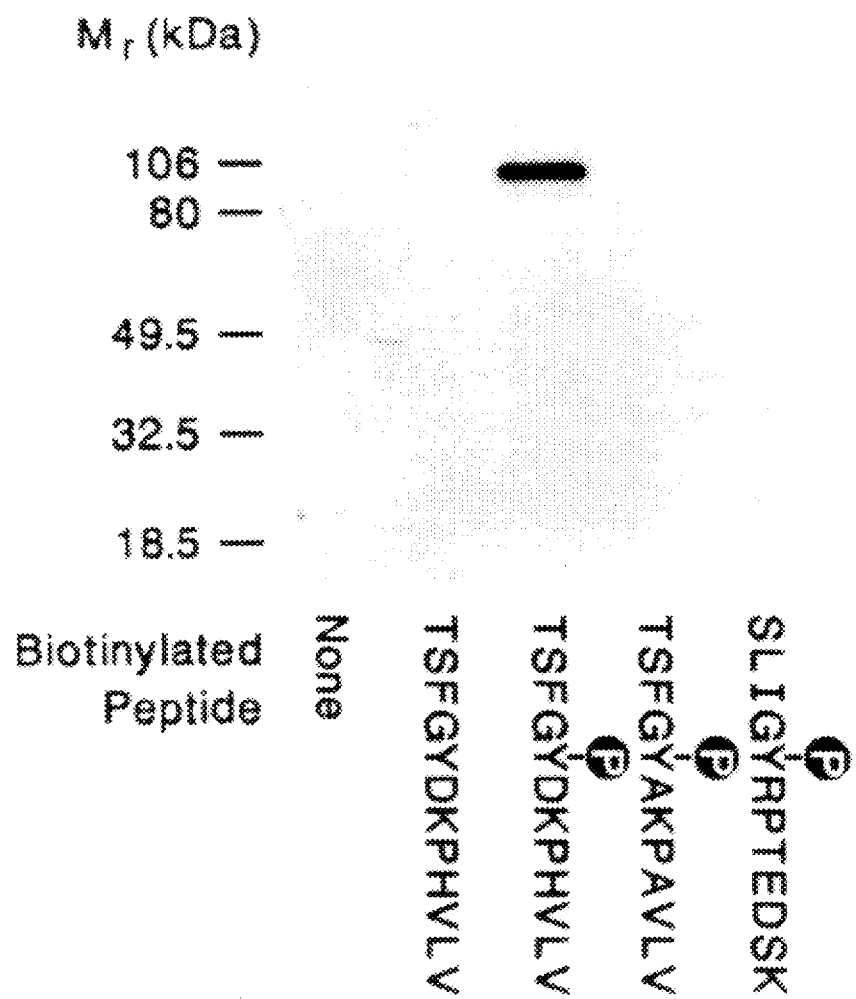
FIG. 6 (Parts A–B) is a western blot showing the analysis of a representative coprecipition experiment (using SEQ ID NOS:4 and 17–19) in which p91 was identified to interact specifically with a peptide containing SEQ ID NO:1.
Figure 6B:
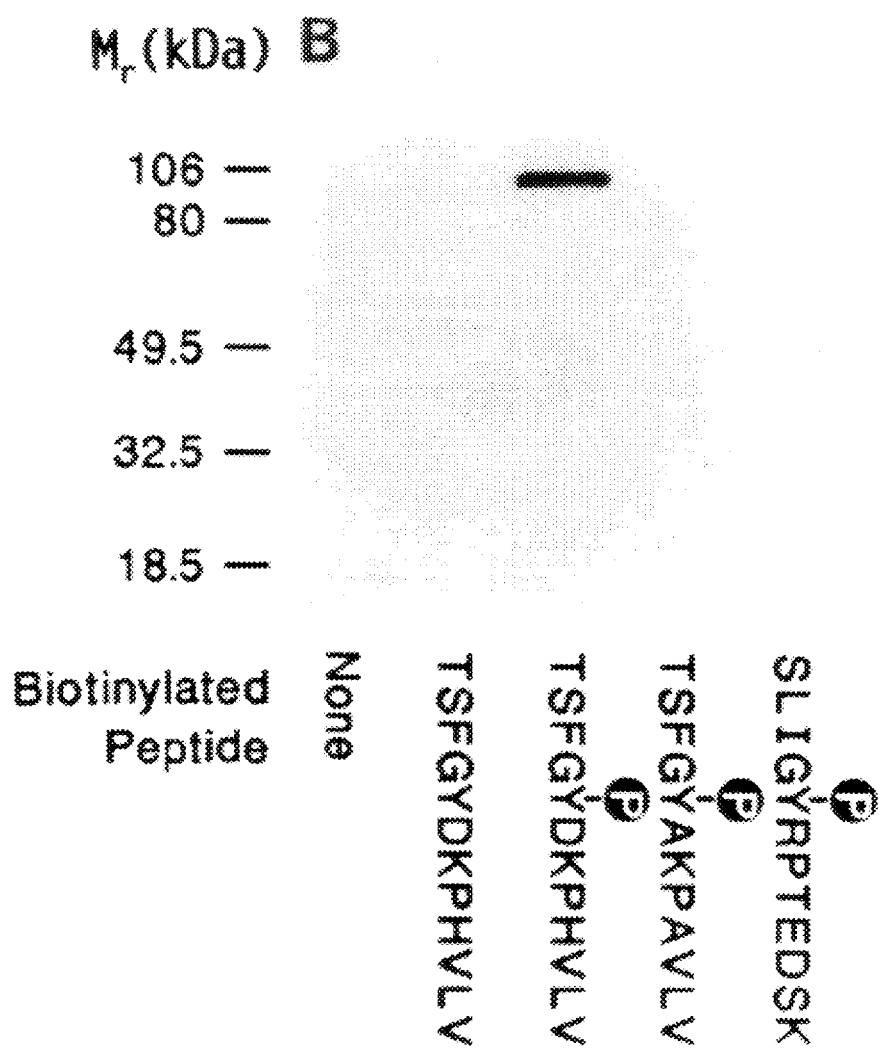

FIG. 6 shows the analysis of a representative coprecipitation experiment in which p91 was identified by western blotting using an antiserum specific for the carboxy terminal portion of the human p91 molecule. Panel A cell homogenates were incubated in the absence of IFNγ, whereas the cell homogenates in Panel B were stimulated with IFNγ. No p91 is precipitated either in the absence of peptide (Lane 1) or in the presence of nonphosphorylated, biotinflated wild type peptide consisting of receptor α chain residues 436–447 (TSFGYDKPHVLV, SEQ ID NO:18, Lane 2). In contrast, p91 is clearly evident in precipitates formed with phosphorylated, biotinylated 436–447 peptide (TSFGY-PO4DKPHVLV, SEQ ID NO:4, Lane 3). The specificity of the interaction between p91 and receptor derived phosphopeptide observed using this direct binding approach corresponds perfectly with that observed using the EMSA functional assay. No interaction of p91 can be detected either with a phosphorylated, biotinylated mutant 436–447 peptide that contains alanine substitutions for the two functionally critical D441 and H444 amino acids (SEQ ID NO:19, Lane 4) or with a phosphorylated, biotinylated peptide derived from a receptor α chain sequence (458–469) that encompasses a functionally unimportant tyrosine residue (Y462, SEQ ID NO:17, Lane 5). Thus, a peptide containing a phosphorylated tyrosine in a sequence corresponding to SEQ ID NO:1 is capable of specifically binding the transcription factor p91 and inhibit its DNA binding activity. It is likely that this phosphotyrosine containing receptor derived sequence, or a derivative or functional equivalent, is useful in inhibiting the development of IFNγ induced biological responses in intact cells.

EXAMPLE 6

This example illustrates the activation of transcription factors STAT1 and STAT3 by IL-10 in extracts of IL-10- receptor transfected BaF3 cells (BaMR), in murine macrophages of the RAW264.7 cell line, in primary murine spenocytes, and in primary murine peritoneal macrophages using the electrophoretic mobility shift and precipitation assays.

Figure 7:
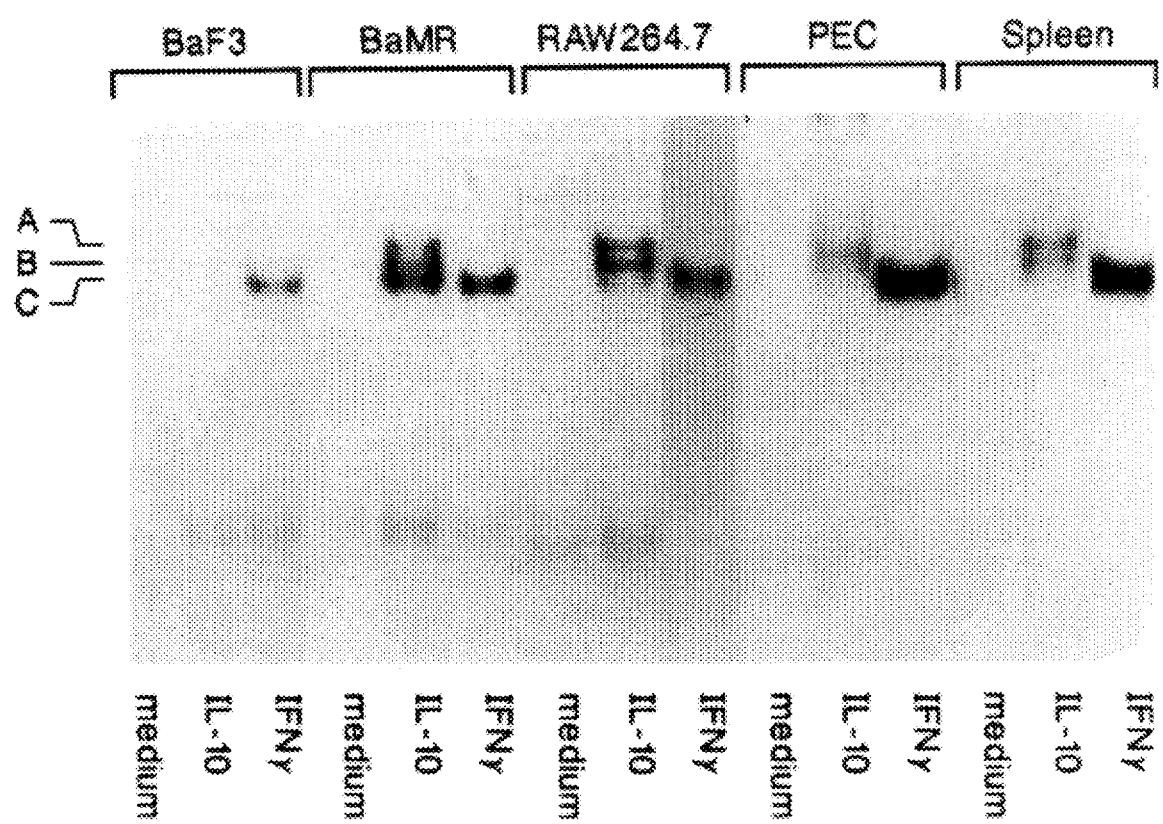
FIG. 7 is a photograph of the results of an electrophoretic mobility shift assay detecting three distinct DNA-protein complexes formed upon IL-10 treatment of extracts from IL-10 receptor negative BaF3 preB-cells, IL-10 receptor transfected BaF3 cells (BaMR), IL-10 receptor positive Raw264.7 macrophages, primary murine splenocytes, and primary murine peritoneal macrophages.

The electrophoretic mobility shift assay was performed according to the methods described in example 4. Specific binding of the IL-10-activated DNA-binding factors to oligonucleotide sequences derived from the Gamma Response Region of the FcγRI gene promoter was determined. The nuclear extracts were untreated, treated with IL-10 at a concentration of 100 ng/ml for 7 minutes at 37° C., or treated with IFNγ at a concentration of 1 ng/ml for 7 minutes at 37° C. DNA-protein complexes were formed and are shown in FIG. 7. The BaF3 receptor-negative cells served as a control. These cells do not express IL-10 receptors and did not activate IL-10 dependent DNA binding complexes whereas these cells were responsive to IFNγ. Three distinct complexes specific for the Gamma Response Region were formed from IL-10-treated nuclear extracts from BaMR preB cells, Raw264.7 macrophages, primary splenocytes and primary peritoneal macrophages. This is indicated in the band A, B, and C in FIG. 7.

These cell types also responded to IFNγ and the expected single protein-DNA complexes were formed from the nuclear extracts. The IFNγ inducible complex showed identical mobility with the lowest of the IL-10 inducible DNA protein complexes (band C). The IL-10 activated DNA binding factors were detectable in cytosolic and nuclear extracts. The complexes were first detectable in nuclear extracts after 1–3 min, were maximal between 7 and 15 minutes after treatment of cells with IL-10 and disappeared within 30–60 minutes. This pattern was distinct from the IFNγ induced complex containing STAT1 (p91) which appeared after 1 minute of stimulation and persisted for 2 to 3 hours.

Figure 8:
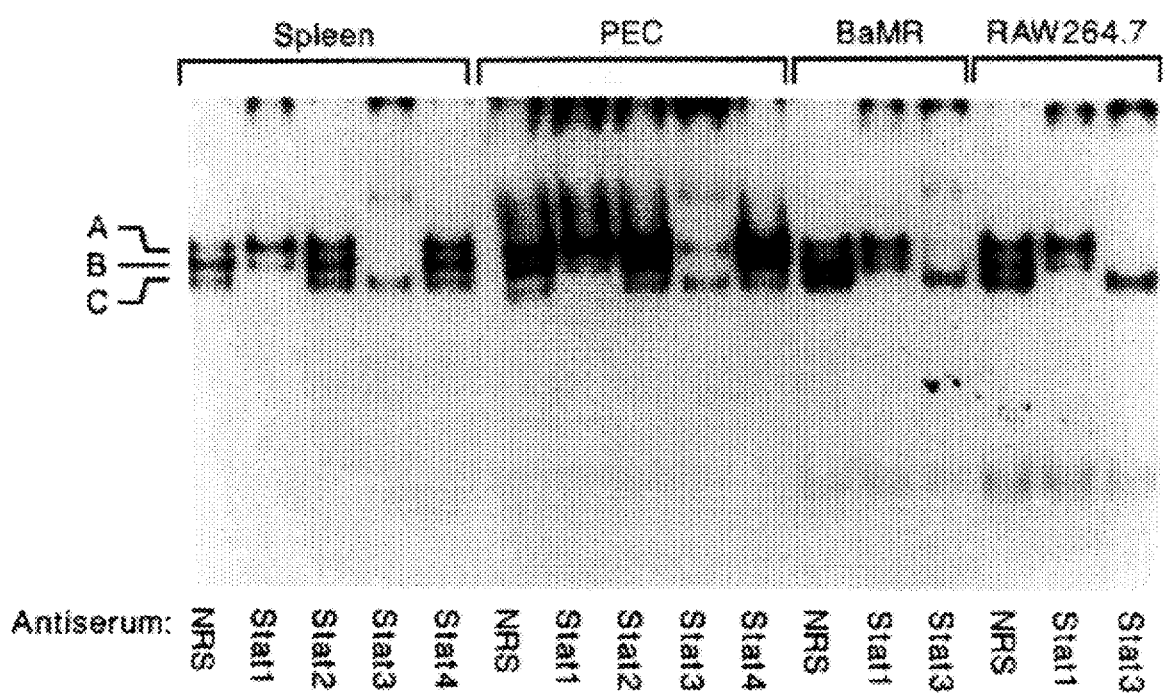
FIG. 8 is a photograph of the results of an electrophoretic mobility shift assay identifying STAT1 and STAT3 as the transcription factors induced by IL-10 in extracts from primary splenocytes, peritoneal macrophages, BaMR cells, and Raw264.7 macrophages following preincubation with STAT1, STAT2, STAT3, or STAT4 specific antisera.

Supershift experiments were performed on nuclear extracts primary splenocytes, primary peritoneal macrophages, BaMR, and Raw264.7 cells treated with IL-10 at a concentration of 100 ng/ml for 7 minutes at 37° C. Nuclear extracts consisting of 5 ug protein were preincubated with 2 μl of a 1:100 dilution of antisera specific for STAT1, STAT2, STAT3, and STAT4, respectively. The reaction was incubated for 1 hour at 4° C. and subsequently run in the mobility shift assay. The results, shown in FIG. 8, indicate that STAT1 is present in the lowest and middle complexes, bands C and B, and STAT3 is present in bands A and B. STAT2 and STAT4 specific antisera did not affect the formation of any of the complexes (FIG. 8).

To further characterize the IL-10 dependent factors that associated with the promoter region of the FcγRI gene, precipitation studies with either biotinylated Gamma-Response-Region probe or the anti-phosphotyrosine antibody 4G10 were performed in nuclear extracts from BaMR preB cells. Procedures were as described above in examples 4 and 5. The biotinylated Gamma-Response-Region probe was prepared on a Beckman Oligo 100 DNA Synthesizer (Beckman, Fullerton, Calif.) using biotin labeled phosphoramidite (Clontech, Palo Alto, Calif.). The double stranded sequence had a Top strand of Biotin-5'ATGTATTTACCAGAA-3' (5'-ATGTATTTACCAGAA-3', SEQ ID NO:12) and Bottom strand of 5'-CTTTTCTGGGAAATA-3' (SEQ ID NO:13). Nuclear extracts consisting of 1 mg protein were untreated, treated with IL-10 at a concentration of 100 ng/ml, or treated with IFNγ at a concentration of 1 ng/ml. The cells were precipitated with either approximately 1 ng of the biotinylated double stranded Gamma-Response-Region oligonucleotide or 5 μg of the phosphotyrosine specific antibody 4G10. Precipitates were sequentially blotted with either STAT1 or STAT3 specific antisera at a concentration of 1 part in 5000 parts PBS (v/v) for 45 minutes at room temperature and goat anti-rabbit peroxicase labeled antisera at a concentration of 1 part in 7500 in PBS (v/v) for 30 minutes at room temperature. The antibody binding was detected with an ECL-kit (Amershem).

Figure 9:
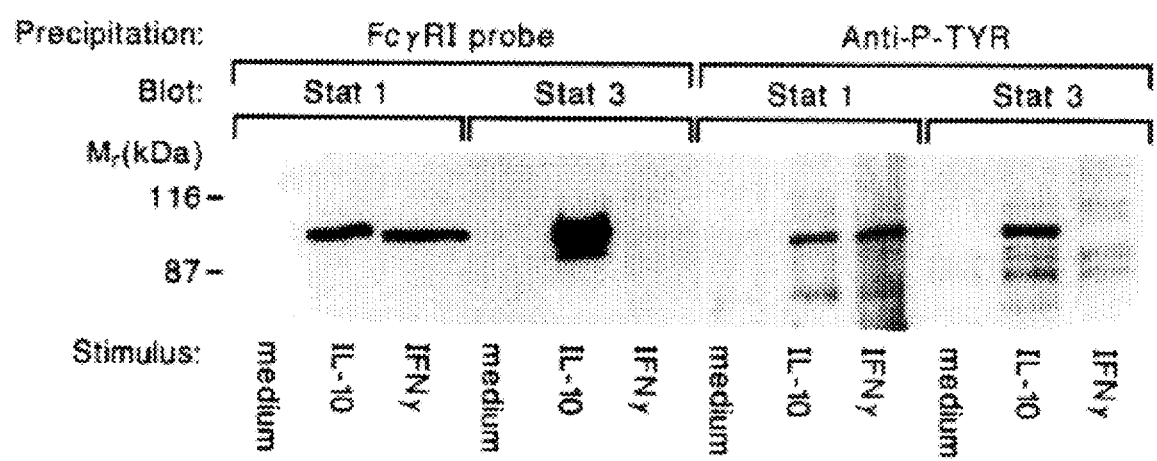
FIG. 9 is a western blot of nuclear extracts of BaMR showing phosphorylated and DNA-associated STAT1 and STAT3 elicited by treatment with IL-10 and IFNγ.

The size and the phosphorylation of the proteins 0 that bound in the promoter region of the FcγkRI gene upon treatment with IL-10 or IFNγ were determined. IL-10 induced the phosphorylation, nuclear localization and DNA binding of both the 91 kD STAT1 (p91) and the 92 kD STAT3 transcription factors (FIG. 9). Accordingly, IL-10 treatment of BaMR cells lead to the phosphorylation of STAT1 and STAT3. However, IFNγ treatment of the cells only caused DNA binding activity and phosphorylation of STAT1 (FIG. 9).

EXAMPLE 7

This example illustrates the association of the STAT3 transcription factor with phosphorylated tyrosines at positions 427 and 477 of the IL-10 receptor intracellular domain and the ability of peptides containing phosphorylated tyrosines at positions 427 and 477 to bind to STAT3.

Having established the activation, phosphorylation and nuclear localization of the STAT1 and STAT3 transcription factors in the IL-10 treated cells, we investigated the importance of the IL-10 receptor intracellular domain tyrosines in the signaling pathway. To further define the functionally critical regions in the IL-10 receptor intracellular domain, synthetic peptides were made which corresponded to the regions of the four potential tyrosine phosphorylation sites in the IL-10 receptor intracellular domain.

Figure 10:
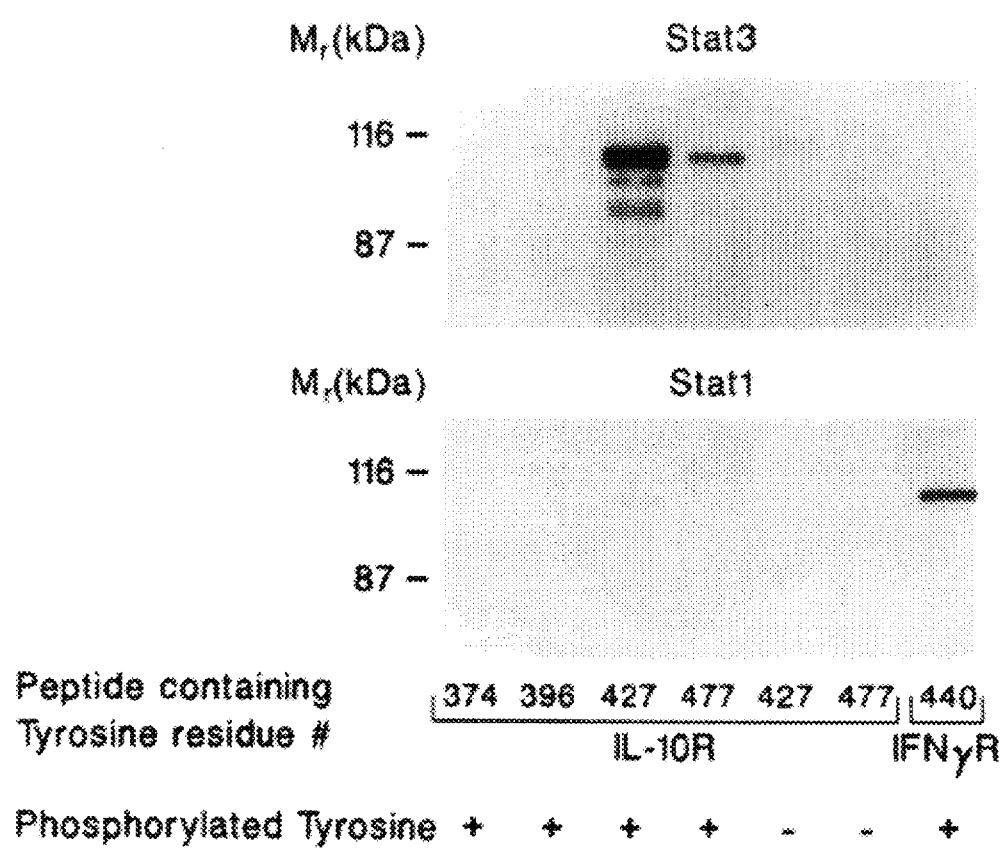
FIG. 10 is a western blot of cytosolic homogenates of BaMR cells in which STAT3 is coprecipitated with biotinylated tyrosine phosphorylated dodecyl peptides having the sequence from the IL-10 receptor that contains either the 427 tyrosine residue (423–434, SEQ ID NO:24, Thr-Phe-Gln-Gly-Xaa-Gln-Lys-Gln-Thr-Arg-Arg-Trp-Lys) or the 477 tyrosine residue (473–484, SEQ ID NO:25, Leu-Ala-Ala-Gly-Xaa-Leu-Lys-Gln-Glu-Ser-Ser-Gln-Gln).

Aminoterminally biotinylated peptides were synthesized comprising 12 amino acids in which the peptides each contained a different region of the IL-10 receptor intracellular domain containing a tyrosine residue. These peptides corresponded to positions 370 to 381 (SEQ ID NO:26, Gln-Gln-Leu-Gly-Xaa-His-Gln-Asp-Gln-Asp-Asp-Ser), 392–403 (SEQ ID NO:27, Gly-Gln-Pro-Lys-Xaa-Thr-Gln-Asp-Ala-Ser-Asp-Leu), 423 to 434 (SEQ ID NO:24, Thr-Phe-Gln-Gly-Xaa-Gln-Lys-Gln-Thr-Arg-Trp-Lys) and 473 to 484 (SEQ ID NO:25, Leu-Ala-Ala-Gly-Xaa-Leu-Lys-Gln-Glu-Ser-Gln-Gly) in which the amino acids identified in the sequence as Xaa in positions 374, 396, 427, and 477 of the respectively peptides are phosphorylated tyrosines. In addition, the sequences 423 to 434 (SEQ ID NO:28, Thr-Phe-Gln-Gly-Tyr-Gln-Lys-Gln-Thr-Arg-Trp-Lys) and 473 to 484 (SEQ ID NO:29, Leu-Ala-Ala-Gly-Tyr-Leu-Lys-Gln-Glu-Ser-Gln-Gly) contained the non-phosphorylated tyrosines in the positions 427, and 477 of the IL-10 receptor intracellular domain. Cytosolic homogenates of BaMR cells were precipitated with the biotinylated 12 amino acid peptides. The peptides containing phosphorylated tyrosines in positions 427 (SEQ ID NO:24) and 477 (SEQ ID NO:25) specifically precipitated the 92 kD, STAT3 protein. In contrast to this, no binding to the STAT3 transcription factor occurred with the peptides containing phosphorylated tyrosines in positions 374 (SEQ ID NO:26) and 396 (SEQ ID NO:27), the peptides containing non-phosphorylated tyrosines in positions 427 (SEQ ID NO:28) and 477 (SEQ ID NO:29) and the phosphorylated peptide corresponding to the amino acid sequences 436 to 447 of the IFNγ receptor α chain intracellular domain (FIG. 10). Whereas both the 427 and the 477 phosphopeptides precipitated the STAT3 transcription factor, none of the phosphopeptides coprecipitated STAT1. The peptide corresponding to the IFNγ receptor intracellular domain containing phosphorylated tyrosine at position 440 served as positive control for precipitation of STAT1 and as negative control for precipitation of STAT3.

These results suggested that STAT3 specifically attaches to the IL-10 receptor, that both tyrosines at positions 427 and 477 are critical in the IL-10 signaling event and that STAT3 is the main transcription factor involved at both IL-10 receptor intracellular tyrosines in positions 427 and 477.

EXAMPLE 9

This example illustrates the functional requirement of association of the STAT3 transcription factor with phosphorylated tyrosines at positions 427 and 477 of the Il-10 receptor intracellular domain and the ability of peptides containing phosphorylated tyrosines at positions 427 and 477 to block activation of STAT3.

Figure 11:
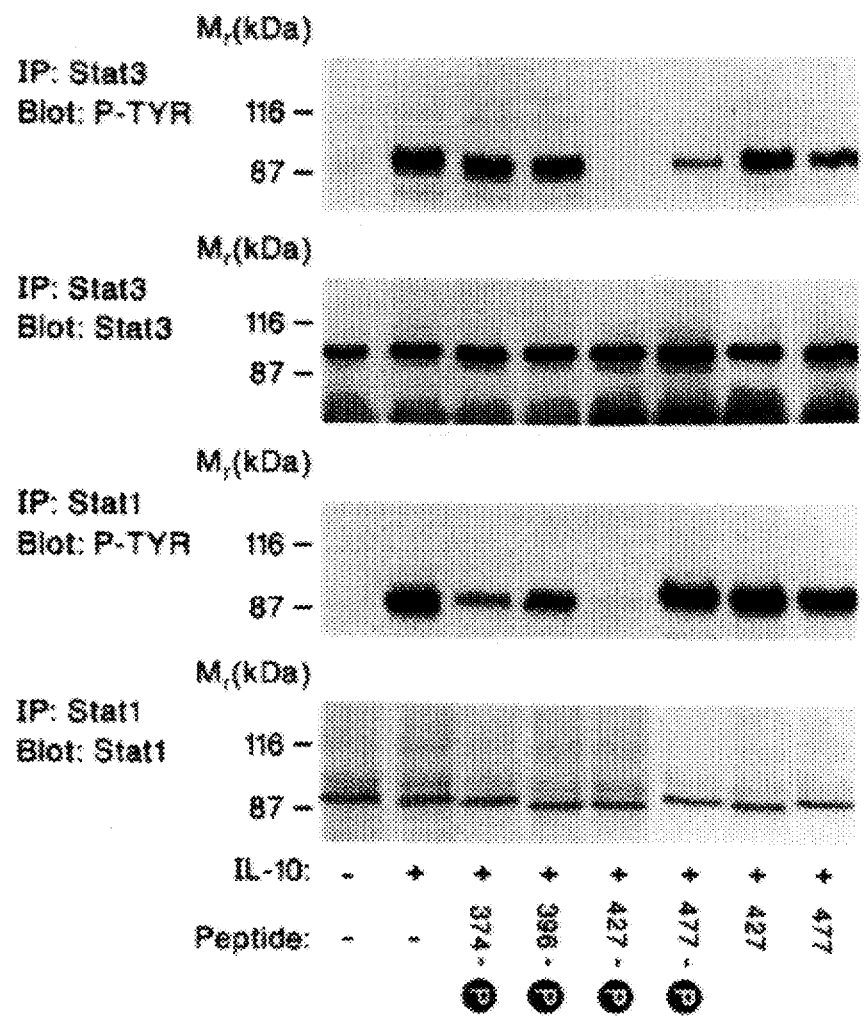
FIG. 11 is a western blot of BaMR cell homogenates stimulated with IL-10 showing the inhibition of STAT3 phosphorylation by dodecyl peptides from the IL-10 receptor containing position 427 or position 477 phosphorylated tyrosine.

BaMR cell homogenates were prepared in a Dounce homogenizer and 18 µg of total protein was incubated without or with IL-10 at a concentration of 100 ng/ml for 15 minutes at 37° C. (FIG. 11, lanes 1 and 2). In lanes 3–8, 18 µg total protein of the BaMR homogenates was incubated for 45 minutes at 4° C. with a 100 µM concentration of the IL-10-receptor peptides having phosphorylated tyrosines at positions 374 (SEQ ID NO:26), 396 (SEQ ID NO:27), 427(SEQ ID NO:24), and 477(SEQ ID NO:25) (lanes 3–6) or 100 µM concentration of the non phosphorylated peptides having tyrosines at positions 427 (SEQ ID NO:28) and 477 (SEQ ID NO:29). Reaction mixtures were stimulated with 100 ng/ml IL-10 as described above and homogenates were precipitated with STAT3 or STAT1 specific antisera. Precipitates were blotted with phosphotyrosine specific antibody RC-20 and reactions developed using the ECL-system. Blots were stripped and reblotted with STAT3 and STAT1 specific antisera, respectively.

Figure 12:
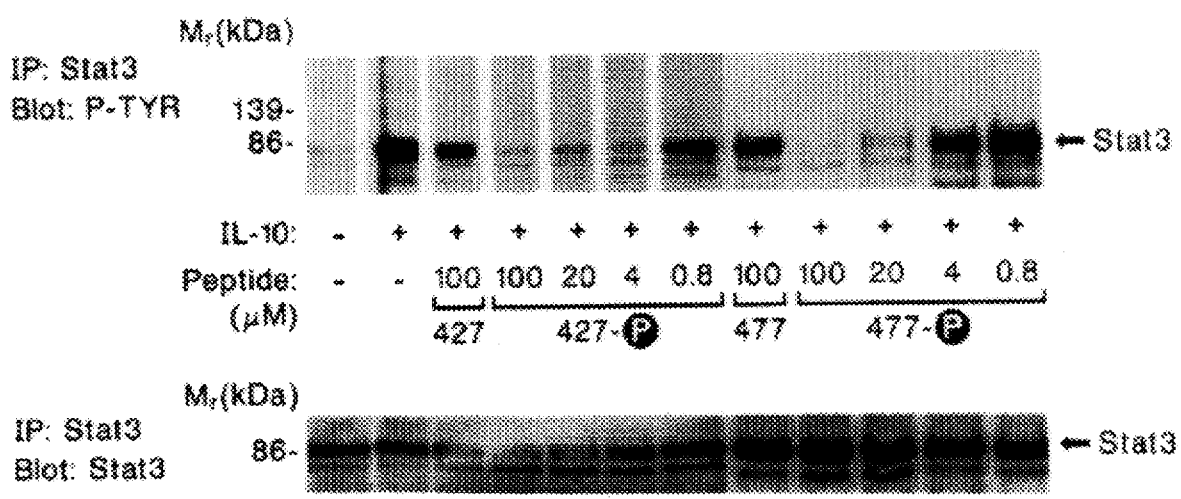
FIG. 12 is a western blot of BaMR cell homogenates stimulated with IL-10 showing the concentration-dependent inhibition of STAT3 phosphorylation by dodecyl peptides from the IL-10 receptor containing position 427 or position 477 phosphorylated tyrosines.

As shown in FIG. 11, phosphorylation of the STAT3 and STAT1 transcription factors was induced upon IL-10 stimulation. Preincubation of the cell homogenates with IL-10 receptor peptides revealed that phosphopeptides having phosphorylated tyrosines at position 427 (SEQ ID NO:24) and position 477 (SEQ ID NO:25) specifically inhibited IL-10 dependent phosphorylation of STAT3. Peptides having phosphorylated tyrosines at position 374 (SEQ ID NO:26) and position 396 (SEQ ID NO:27) as well as the nonphosphorylated peptides in positions 427 and 477 (SEQ ID NOS:19C and 19D, respectively) did not affect STAT3 phosphorylation. The peptide having a phosphorylated tyrosine at position 427 (SEQ ID NO:24) was 5 to 10 fold more potent in inhibiting STAT3 phosphorylation than and the peptide having a phosphorylated tyrosine at position 477 (SEQ ID NO:25) (FIG. 12).

These results were in agreement with the results of precipitation experiments employing increasing concentrations of each of the corresponding two biotinylated phosphopeptides. In these experiments 0.8 µM of the biotinylated peptide having a phosphorylated tyrosine at position 427 (SEQ ID NO:24) were sufficient to precipitate STAT3 whereas 4–20 µM of the peptide having a phosphorylated tyrosine at position 477 (SEQ ID NO:25) were needed to precipitate comparable amounts of STAT3 (data not shown).

Having established the association of the IL-10 receptor intracellular domain with STAT3 and the functional importance of the phosphotyrosine residues at positions 427 and 477 for the activation of STAT3, we determined the role of the IL-10 receptor intracellular domain for the activation of STAT1. Precipitation and phosphorylation studies were repeated and homogenates precipitated with the STAT1 antisera. The results of these experiments showed that none of the IL-10 receptor peptides precipitated STAT1.

EXAMPLE 10

This example illustrates the in vivo effectiveness of compositions binding to p91 and inhibiting IFNγ by evaluating the blocking of generation of activated macrophages and resolution of infection in mice challenged with *Listeria monocytogenes*.

Endogenous IFNγ is known to be required for the generation of activated macrophages and the resolution of *L. monocytogenes* infections in mice (Buchmeier and Schreiber, *Proc Natl Acad Sci* 82:7404–7408, 1985 which is incorporated by reference). This example utilizes this model to illustrate the in vivo activity of transcription-factor binding compositions.

Six- to 8-week old mice are used such as from the strain C3HeB/FeJ obtained from the breeding colony at the Research Institute of Scripps Clinic or Balb/c mice obtained from Jackson Laboratories. *Listeria monocytogenes* is injected intraperitoneally and recovered from splenic homogenates by inoculation into cultures of brain-heart infusion broth (Baltimore Biological Laboratory, Cockeysville Md.). To standardize the infecting dose of Listeria, frozen aliquots of an expanded bacterial culture were thawed, washed in phosphate-buffered saline, and adjusted to give an infecting dose of 3–6×10$^3$ colony-forming units in 0.3 ml. Colony counts of the inoculum are routinely performed on brain-heart infusion agar (Baltimore Biological Laboratory. Bacteria in the spleens of infected mice are quantitated by colony counts of splenic homogenates in Hanks' balanced salt solution plated on brain-heart infusion agar. Bacteria in the peritoneal cavity were assessed by sonicating an aliquot of the peritoneal wash and then plating on brain heart-infusion agar.

Mice are infected with 2×10$^3$ colony forming units of Listeria monocytogenese, i.p., and 24 hours later are injected i.p. with the peptide composition of SEQ ID NO:3 or SEQ ID NO:3 in a suitable pharmaceutical preparation. Twenty-four hours later the peritoneal cells are harvested and tested for the presence of primed or activated macrophages by using various doses of heat-killed *Listeria monocytogenese* as the triggering signal. Macrophage activation is quantitated by measuring the ability of macrophages to lyse $^{111}$In-labeled P815 mastocytoma cells according to the method of Schreiber et al. (*J Exp Med* 156:677–689, 1982 which is incorporated by reference). Whereas cells from uninfected or sham-infected mice produce only minimal cell lysis, cells derived from Listeria-infected mice produce substantial specific tumor cell lysis over a wide range of triggering signal concentrations of heat-killed Listeria. Macrophages from Listeria-infected mice treated With peptide compositions display a diminished specific tumor cell lysis compared to untreated Listeria-infected mice.

In testing for resolution of the Listeria infection, mice are infected with 6×10$^3$ colony forming units of *Listeria monocytogenes* and 24 hours later left untreated or injected i.p. with a peptide composition of SEQ ID NO:3 or SEQ ID NO:4 in a suitable pharmaceutical preparation. At 4 and 6 days after infection, groups of mice are sacrificed and bacterial counts are made of the peritoneal cavities and spleen. Although relatively low levels of microorganism are found in peritoneal cavity and spleen of untreated animals,

23 substantially greater levels are found in the peritoneal cavity and spleen of mice treated with the peptide composition. Survival in treated and untreated groups is also monitored.

EXAMPLE 11

This example illustrates the effect of IL-10 inhibition by peptides and derivatives binding to the STAT3 transcription factor to block IL-10-mediated protection from endotoxin shock.

It is known that exogenous administration of IL-10 confers protection to mice from lethal endotoxemia on challenge with bacterial lipopolysaccharide (Howard et al., *J Exp Med* 177:1205–1208, 1993; Gerard et al., *J Exp Med* 177:547–550, 1993 all of which are incorporated by reference). This model can, therefore, be used to evaluate the in vivo activity of the STAT3-binding proteins and derivatives.

Eight- to 10-week-old BALB/c mice are obtained from Jackson Laboratories. Lipopolysaccharide is obtained from Sigma Immunochemicals (St. Louis, Mo.). Mice are injected intraperitoneally with 100 µl volume containing doses of endotoxin ranging from 250 to 425 µg. Survival of the mice at 2 hours after lipopolysaccharide administration is determined and a $LD_{90}$ dose is calculated and used in subsequent tests. Recombinant murine IL-10 is diluted in PBS containing 0.1% BSA and administered to mice concurrently with the lipopolysaccharide at various concentrations in a total volume of 100 µl. Percent survival is calculated for different concentrations from 0.05 to 10 µg IL-10.

To determine the effect of the peptides and derivatives binding STAT3 transcription factor, SEQ ID NO:24 or SEQ ID NO:25 is administered to the mice in appropriate pharmaceutical vehicle prior to challenge with lipopolysaccharide with concomitantly administered IL-10. Survival rates are compared in groups receiving lipopolysaccharide alone, lipopolysaccharide with IL-10, and lipopolysaccharide with IL-10 following pretreatment with Sequence ID NO:19C.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

---

What is claimed is:

1. A composition of matter comprising an isolated peptide or a derivative thereof wherein the peptide contains an amino acid sequence derived from a receptor for a cytokine, wherein the peptide contains a phosphorylated tyrosine, and wherein the protein specifically binds to a member of the STAT family of transcription factors to inhibit activation of the transcription factor by the cytokine.

2. The composition of claim 1 wherein the member of the STAT family transcription factor is selected from the group consisting of STAT 1, STAT 2, STAT 3, STAT 4, STAT 5, and IL-4 STAT.

3. The composition of claim 1 wherein the peptide contains the sequence of SEQ ID NO:20 (Xaa-Gln-Lys-Gln-Thr, where Xaa is a phosphorylated tyrosine) or SEQ ID NO:21 (Xaa-Leu-Lys-Gln-Glu, where Xaa is a phosphorylated tyrosine) or a derivative thereof.

4. A method for identifying a derivative of the isolated peptide of claim 1 comprising detecting the inhibition of the binding of said peptide to a STAT family transcription factor by said derivative.

5. The composition of claim 3 wherein said peptide or derivative thereof specifically binds to transcription factor STAT3 in a manner inhibiting its transcriptional activating properties.

6. The composition of claim 5 wherein the cytokine is interleukin-10 (IL-10).

7. The composition of claim 6 wherein said peptide contains the sequence of SEQ ID NO:24 (Thr-Phe-Gln-Gly-Xaa-Gln-Lys-Gln-Thr-Arg-Arg-Trp-Lys, where Xaa is phosphorylated tyrosine) or SEQ ID NO:25 (Leu-Ala-Ala-Gly-Xaa-Leu-Lys-Gln-Glu-Ser-Ser-Gln-Gln, where Xaa is phosphorylated tyrosine) or a derivative thereof.

8. The method of claim 4 wherein the isolated peptide contains SEQ ID NO:24 or SEQ ID NO:25.

\* \* \* \* \*

UNITED STATES PATENT AND TRADEMARK OFFICE
CERTIFICATE OF CORRECTION

PATENT NO. : 5,731,155
DATED : March 24, 1998
INVENTOR(S) : Schreiber et al.

It is certified that error appears in the above-indentified patent and that said Letters Patent is hereby corrected as shown below:

Column 37, claim 1, line 5 the word "protein" should read --peptide--.

Signed and Sealed this

Twenty-third Day of June, 1998

Attest:

BRUCE LEHMAN

*Attesting Officer*  *Commissioner of Patents and Trademarks*